United States Patent
Ryoo et al.

(10) Patent No.: US 10,646,203 B2
(45) Date of Patent: May 12, 2020

(54) ULTRASOUND DIAGNOSIS METHOD AND APPARATUS FOR ANALYZING CONTRAST ENHANCED ULTRASOUND IMAGE

(71) Applicant: SAMSUNG MEDISON CO., LTD., Hongcheon-gun, Gangwon-do (KR)

(72) Inventors: Ho-jin Ryoo, Gangwon-do (KR); Jong-sik Kim, Gangwon-do (KR); Jin-yong Lee, Gangwon-do (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 765 days.

(21) Appl. No.: 15/082,174

(22) Filed: Mar. 28, 2016

(65) Prior Publication Data
US 2017/0100101 A1    Apr. 13, 2017

(30) Foreign Application Priority Data

Oct. 8, 2015   (KR) .................. 10-2015-0141637

(51) Int. Cl.
*A61B 8/08*    (2006.01)
*A61B 8/14*    (2006.01)
*A61B 8/00*    (2006.01)

(52) U.S. Cl.
CPC ............ *A61B 8/5215* (2013.01); *A61B 8/085* (2013.01); *A61B 8/14* (2013.01); *A61B 8/465* (2013.01); *A61B 8/469* (2013.01); *A61B 8/481* (2013.01); *A61B 8/5207* (2013.01); *A61B 8/5276* (2013.01)

(58) Field of Classification Search
None
See application file for complete search history.

(56) References Cited

U.S. PATENT DOCUMENTS

| | | | |
|---|---|---|---|
| 6,193,660 B1* | 2/2001 | Jackson | A61B 8/00 600/443 |
| 7,593,554 B2* | 9/2009 | Miller | A61B 8/463 382/128 |
| 2008/0214934 A1* | 9/2008 | Lee | A61B 8/481 600/437 |
| 2008/0319309 A1* | 12/2008 | Bredno | A61B 5/0275 600/420 |

(Continued)

FOREIGN PATENT DOCUMENTS

| | | |
|---|---|---|
| CN | 103860201 A | 6/2014 |
| JP | 6269424 A | 9/1994 |

(Continued)

OTHER PUBLICATIONS

Communication dated Feb. 20, 2017, issued by the European Patent Office in counterpart European Application No. 16162999.3.

*Primary Examiner* — Katherine L Fernandez
*Assistant Examiner* — Yi-Shan Yang
(74) *Attorney, Agent, or Firm* — Sughrue Mion, PLLC

(57) ABSTRACT

Provided are an ultrasound diagnosis apparatus and method for analyzing a contrast enhanced ultrasound image. The ultrasound diagnosis apparatus and method determine, by analysis, causes of defects in a frame of an ultrasound image based on a time intensity curve and allow visual display of the defective frame based on the determined causes. Furthermore, the ultrasound diagnosis method and apparatus may provide a user interface for quick access to causes of defects in a frame of the ultrasound image and to a position of the defective frame.

22 Claims, 22 Drawing Sheets

(56) References Cited

U.S. PATENT DOCUMENTS

| | | | |
|---|---|---|---|
| 2009/0030322 A1 | 1/2009 | Fujiwara et al. | |
| 2010/0298706 A1* | 11/2010 | Averkiou | A61B 8/481 600/443 |
| 2011/0075904 A1* | 3/2011 | Yoshikawa | A61B 8/06 382/131 |
| 2011/0150309 A1* | 6/2011 | Barfett | G06T 7/33 382/131 |
| 2013/0116565 A1* | 5/2013 | Miyama | A61B 8/481 600/443 |
| 2013/0197363 A1* | 8/2013 | Rankin | A61B 18/1492 600/439 |
| 2015/0371379 A1* | 12/2015 | Averikou | A61B 8/06 382/128 |
| 2016/0242741 A1* | 8/2016 | Wan | A61B 8/06 |

FOREIGN PATENT DOCUMENTS

| | | |
|---|---|---|
| JP | 2009-028194 A | 2/2009 |
| JP | 2011-045449 A | 3/2011 |
| JP | 2012-179325 A | 9/2012 |
| KR | 10-1206307 B1 | 11/2012 |
| KR | 10-1480434 B1 | 1/2015 |
| WO | 2007069166 A2 | 6/2007 |
| WO | 2009093211 A1 | 7/2009 |

* cited by examiner

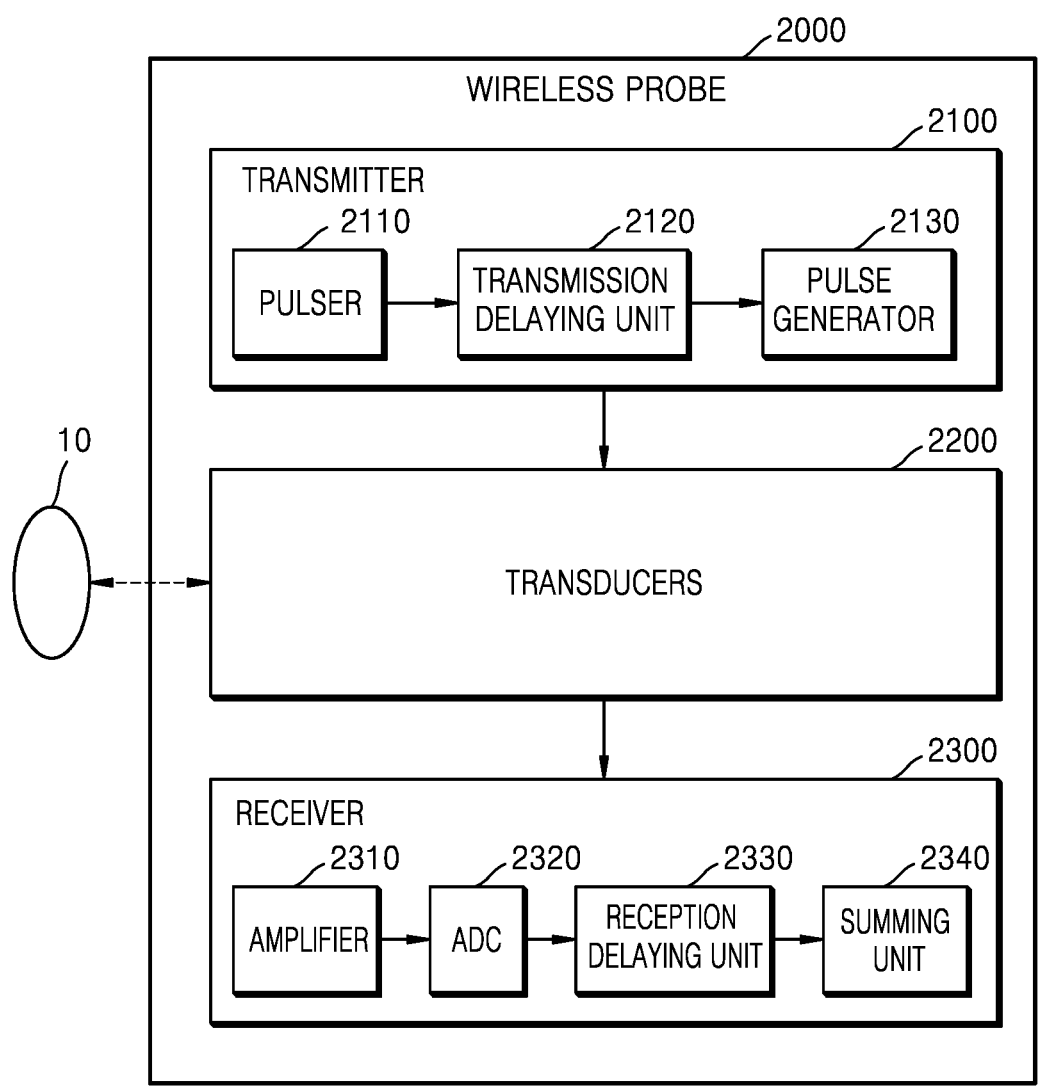

ULTRASOUND DIAGNOSIS METHOD AND APPARATUS FOR ANALYZING CONTRAST ENHANCED ULTRASOUND IMAGE

CROSS-REFERENCE TO RELATED APPLICATION

This application claims the benefit of Korean Patent Application No. 10-2015-0141637, filed on Oct. 8, 2015, in the Korean Intellectual Property Office, the disclosure of which is incorporated herein in its entirety by reference.

BACKGROUND

1. Field

The present disclosure relates to methods and apparatuses for analyzing a contrast enhanced ultrasound (CEUS) image, and more particularly, to methods and apparatuses for analyzing a type of motion of an object in a CEUS image and a change in a size of the object.

2. Description of the Related Art

Due to its non-invasive and non-destructive nature, an ultrasound system has become widely used in many medical fields that require information about the inside of an object. The ultrasound system also plays a critical role in medical diagnosis since it can provide high-resolution images of an inner area of an object to a medical practitioner without the need for performing a surgical procedure to directly incise the object for observation.

Among imaging methods using an ultrasound system, contrast enhanced ultrasound (CEUS) imaging involves administration of contrast agents to an object. Examination using a CEUS image allows a user to quantitatively determine whether an object such as a tumor is malignant or benign by observing a tendency of image signal values of the object over time after injection of a contrast agent into the object. In CEUS examination, analysis using a time intensity curve (TIC) may be performed. By using a TIC, it is possible to calculate an average image signal value of pixels within a region of interest (ROI) set in an ultrasound image and thus observe a change in contrast agent concentration over time. However, defects that may cause errors in analysis based on a TIC, such as a deviation of an object away from an ROI or a change in size of the object, may occur in frames of an ultrasound image. It is time consuming for a user to delete the defective frames, and thus efficiency in examination may be degraded.

SUMMARY

Provided are ultrasound diagnosis methods and apparatuses for analyzing a contrast enhanced ultrasound (CEUS) image that allow causes of defects in a frame of an ultrasound image to be determined based on a time intensity curve and provide a user interface for quick access to the defective frame.

Additional aspects will be set forth in part in the description which follows and, in part, will be apparent from the description, or may be learned by practice of the presented embodiments.

According to an aspect of an embodiment, an ultrasound diagnosis apparatus for analyzing a contrast enhanced ultrasound image with respect to an object to which an ultrasound contrast medium has been administered, the contrast enhanced ultrasound image being obtained by transmitting ultrasound waves to the object and receiving echo signals reflected from the object, includes: an ultrasound image processor configured to set a region of interest (ROI) in the ultrasound image and acquire a time intensity curve representing an intensity value for each of ultrasound image frames in the set ROI and a fitting curve representing a tendency of the time intensity curve according to a preset mathematical model; an ultrasound image analyzer configured to analyze a type of movement of the object and a change in size of the object based on a difference between the time intensity curve and the fitting curve; and a user input unit configured to display a user interface that receives a user input for selecting frames of the ultrasound image related to the movement of the object and the change in size of the object.

The ultrasound image analyzer may analyze at least one of a simple movement that is a temporary deviation of the object away from the ROI, a periodic movement that is a periodic deviation of the object away from the ROI, and the change in size of the object in the ROI.

The ultrasound image analyzer may recognize a state in which an ultrasound probe is not in contact with the object.

The user input unit may display, based on a result of the analyzing, a graphics user interface (GUI) corresponding to each of the type of movement of the object, the change in size of the object, and non-contact between an ultrasound probe and the object.

The ultrasound diagnosis apparatus may further include a display configured to display a frame of the ultrasound image related to at least one of the type of movement of the object and the change in size of the object received via the user interface.

The ultrasound image analyzer may calculate a difference between the time intensity curve and the fitting curve and determine that the object has deviated away from the ROI when the calculated difference exceeds a threshold value.

The ultrasound image analyzer may determine that the object has periodically deviated away from the ROI when the calculated difference periodically exceeds the threshold value.

The threshold value may be determined based on an average of differences between the time intensity curve and the fitting curve for frames of the ultrasound image and a standard deviation of the differences.

The ultrasound diagnosis apparatus may further include a display configured to display the time intensity curve, the fitting curve, a difference curve representing a difference between the time intensity curve and the fitting curve for each of ultrasound image frames, and a threshold curve representing a threshold value for each of ultrasound image frames.

The ultrasound image processor may set an additional ROI, which is larger than and includes the ROI, in the ultrasound image, and the ultrasound image analyzer may acquire a time intensity curve for each ultrasound image frame within the additional ROI and analyze a change in intensity values of the ultrasound image within the additional ROI based on the acquired time intensity curve for the additional ROI.

The ultrasound image analyzer may analyze movement of the object included in the additional ROI and a change in size of the object based on a result of the analyzing.

According to an aspect of another embodiment, a method of analyzing an ultrasound image with respect to an object to which an ultrasound contrast medium has been administered, the ultrasound image being obtained by transmitting ultrasound waves to the object and receiving echo signals reflected from the object, includes: setting an ROI in the ultrasound image; acquiring a time intensity curve representing an average of intensity values for each of ultrasound image frames in the set ROI and a fitting curve representing a tendency of the time intensity curve according to a preset mathematical model; analyzing a type of movement of the object included in the ROI and a change in size of the object based on the acquired time intensity curve and fitting curve; and displaying a user interface configured to receive a user input for selecting frames of the ultrasound image in which the movement of the object and the change in size of the object occur.

The method may further include: receiving via the user interface a user input for selecting at least one of the type of movement of the object and the change in size of the object; and displaying, based on the user input, a frame of the ultrasound image related to the movement of the object and the change in size of the object.

The analyzing of the type of movement of the object and the change in size of the object may include analyzing at least one of a simple movement that is a temporary deviation of the object away from the ROI, a periodic movement that is a periodic deviation of the object away from the ROI, and the change in size of the object in the ROI.

The analyzing of the type of movement of the object and the change in size of the object may include recognizing a state in which an ultrasound probe is not in contact with the object.

The recognizing of the state in which the ultrasound probe is not in contact with the object may include: determining a frame of the ultrasound image at which the time intensity curve for the ultrasound image included in the ROI has a value of 0; and determining the frame of the ultrasound image as a frame captured when the ultrasound probe is not in contact with the object.

The analyzing of the type of movement of the object and the change in size of the object may include: calculating a difference between the time intensity curve and the fitting curve; and determining that the object has deviated away from the ROI when the calculated difference exceeds a threshold value.

The threshold value may be determined based on an average of differences between the time intensity curve and the fitting curve for frames of the ultrasound image and a standard deviation of the differences.

The analyzing of the type of movement of the object and the change in size of the object may include: setting an additional ROI, which is larger than and includes the ROI, in the ultrasound image; acquiring a time intensity curve for each ultrasound image frame included in the additional ROI; and analyzing a change in intensity values of the ultrasound image included in the additional ROI based on the acquired time intensity curve for the additional ROI.

The analyzing of the type of movement of the object and the change in size of the object may further include analyzing the movement of the object and the change in size of the object based on a result of the analyzing of the change in intensity values of the ultrasound image included in the additional ROI.

The analyzing of the type of movement of the object and the change in size of the object may include analyzing, based on the acquired time intensity curve for the additional ROI, whether the intensity values of the ultrasound image included in the additional ROI periodically change.

The displaying of the user interface may include displaying a position the frame of the ultrasound image in which the movement of the object and the change in size of the object occur in such a manner as to overlap the time intensity curve.

The method may further include displaying the frame of the ultrasound image selected based on the user input.

According to an aspect of another embodiment, a non-transitory computer-readable recording medium has recorded thereon a program for executing on a computer the method of analyzing an ultrasound image of an object, which includes: setting an ROI in the ultrasound image; acquiring a time intensity curve representing an average of intensity values for each of ultrasound image frames in the set ROI and a fitting curve representing a tendency of the time intensity curve according to a preset mathematical model; analyzing a type of movement of the object included in the ROI and a change in size of the object based on the acquired time intensity curve and fitting curve; and displaying a user interface configured to receive a user input for selecting frames of the ultrasound image in which the movement of the object and the change in size of the object occur

BRIEF DESCRIPTION OF THE DRAWINGS

These and/or other aspects will become apparent and more readily appreciated from the following description of the embodiments, taken in conjunction with the accompanying drawings in which:

FIG. 17 is a block diagram of a configuration of a wireless probe according to an embodiment.

DETAILED DESCRIPTION

Figure 1:
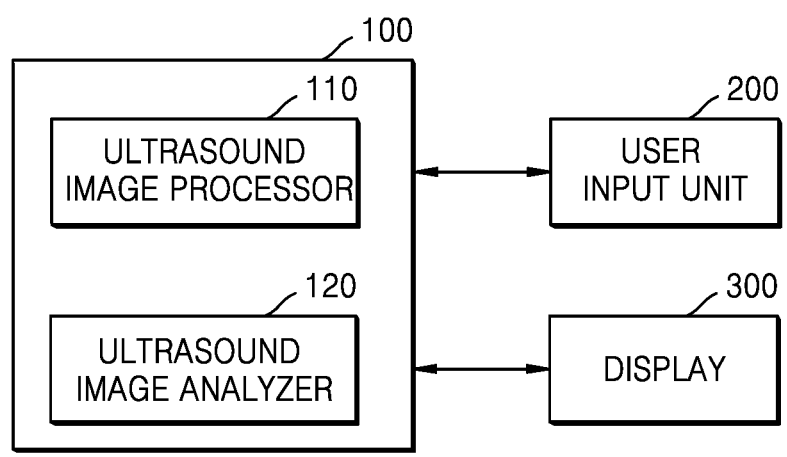
FIG. 1 is a block diagram of a configuration of an ultrasound diagnosis apparatus according to an embodiment.

Features of one or more embodiments of the present inventive concept and methods of accomplishing the same may be understood more readily by reference to the following detailed description of embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present inventive concept will only be defined by the appended claims.

Terms used herein will now be briefly described and then one or more embodiments of the present inventive concept will be described in detail.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of the disclosure. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments of the present disclosure means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of a program code, drivers, firmware, micro codes, circuits, data, a database, data structures, tables, arrays, or variables. A function provided by the components and "units" may be associated with the smaller number of components and "units", or may be divided into additional components and "units". As used herein, the term "and/or" includes any and all combinations of one or more of the associated listed items Expressions such as "at least one of," when preceding a list of elements, modify the entire list of elements and do not modify the individual elements of the list.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Furthermore, in the present specification, the terms "first", "second", "1-1", etc. are only used to distinguish one component, element, image, pixel, or patch from another component, element, object, image, pixel, or patch. Thus, these terms are not limited to representing the order or priority among elements or components.

Embodiments will now be described more fully hereinafter with reference to the accompanying drawings so that they may be easily implemented by one of ordinary skill in the art. In addition, parts not related to the present inventive concept are omitted to clarify the description of embodiments.

FIG. 1 is a block diagram of a configuration of an ultrasound diagnosis apparatus 1000 according to an embodiment.

Referring to FIG. 1, the ultrasound diagnosis apparatus 1000 according to the present embodiment may include a processor 100, a user input unit 200, and a display 300.

The processor 100 may include an ultrasound image processor 110 and an ultrasound image analyzer 120. The processor 100 may be an operational device that generates an ultrasound image by performing scan conversion on ultrasound image data received from an ultrasound transceiver (not shown) and has an operation capability of converting image signal values of the generated ultrasound image into numerical values. For example, the processor 100 may be one hardware device from among a central processing unit (CPU), a microprocessor, and a graphics processing unit (GPU).

The ultrasound image processor 110 may receive information of echo signals reflected from an object to obtain an ultrasound image. The ultrasound image processor 110 may process ultrasound image data according to an image display mode. The ultrasound image processor 110 may acquire brightness (B) mode data by performing processing such as amplification, logarithmic compression, and envelope detection on echo signals received from the ultrasound transceiver or obtain contrast enhanced mode data by intravenously injecting ultrasound contrast medium containing microbubbles into the object. The ultrasound image processor 110 may use strong nonlinear effects of ultrasound contrast medium in a contrast enhanced ultrasound (CEUS) mode. Due to the nonlinear effects of ultrasound contrast medium, waves reflected from microbubbles are greatly distorted compared to incident waves, which causes generation of harmonic components. The ultrasound image processor 110 may use a contrast harmonic imaging technique based on the above characteristics, in which fundamental waves are suppressed by imaging a harmonic wave having a frequency that is twice the frequency of the fundamental waves while a contrast medium is further enhanced. By using the contrast harmonic imaging technique, it is possible to obtain an image in which waves reflected from a contrast medium are enhanced since waves reflected from microbubbles contain more harmonic wave components than waves reflected from a biological tissue.

The ultrasound image processor 110 may set a region of interest (ROI) in an obtained ultrasound image. The ultrasound image processor 110 may set an ROI in a B mode ultrasound image acquired from B mode image data and/or in a CEUS image. According to an embodiment, the ultrasound image processor 110 may set an ROI in an object depicted in an ultrasound image based on a user input received from the user input unit 200. However, embodiments are not limited thereto, and the ultrasound image processor 110 may detect an object such as a tumor and automatically set an ROI along an edge of the tumor.

The ultrasound image processor 110 may generate a TIC representing an image signal value for each frame of an ultrasound image within a set ROI. In detail, the ultrasound image processor 110 may extract image signal values, e.g., intensity values, of respective pixels of the ROI in the ultrasound image, convert the intensity values of the respective pixels into numerical values, and calculate a total sum and an average of the intensity values of the pixels for each ultrasound image frame. The ultrasound image processor 110 may generate a graph showing the calculated average of intensity values of pixels in the ROI for each ultrasound image frame and obtain a TIC based on the graph. The TIC is mainly used for an ultrasound examination using ultrasound contrast medium.

The ultrasound image processor 110 may also generate a fitting curve representing the tendency of the TIC. The ultrasound image processor 110 may analyze a tendency of the TIC based on a predefined mathematical model and generate a graph showing values corresponding to the analyzed tendency of frames of an ultrasound image. According to an embodiment, the predefined mathematical model may include at least one of a polynomial model, exponential rise, gamma variant, and a sigmoidal model. In detail, the ultrasound image processor 110 may generate a fitting curve representing the tendency of the TIC based on a user input for selecting at least one from among a polynomial model, exponential rise, gamma variant, and a sigmoidal model. However, embodiments are not limited thereto, and the ultrasound image processor 110 may generate a fitting curve based on a mathematical model preset among the above mathematical models. Since techniques for generating a fitting curve representing the tendency of a TIC based on at least one of the polynomial model, exponential rise, gamma variant and sigmoidal model are well known to those of ordinary skill in the art, detailed descriptions thereof will be omitted here.

The ultrasound image analyzer 120 may analyze a type of movement of an object included in an ROI and a change in size of the object based on a difference between a TIC and a fitting curve generated by the ultrasound image processor 110 with respect to an ultrasound image in the ROI. In one embodiment, the ultrasound image analyzer 120 may analyze whether the object deviates outside the ROI, whether the object moves periodically, whether a size of the object changes, and whether an ultrasound probe is not in contact with the object. Furthermore, the ultrasound image analyzer 120 may detect a frame of an ultrasound image generated for each case, i.e., cases where it is determined that the object has deviated outside the ROI, where it is determined that the object has moved periodically, where it is determined that the size of the object has changed, and where it is determined that the ultrasound probe has not been in contact with the object, and define the detected frame as a defective frame.

Methods of analyzing a movement of an object included in an ROI and a change in size of the object based on a TIC and a fitting curve will be described in more detail below with reference to FIGS. 3 through 15.

The user input unit 200 may receive a user input for selecting a frame of an ultrasound image related to movement of the object or a change in size of the object. According to an embodiment, the user input unit 200 may display a user interface (UI) configured to select a frame having a defect associated with at least one of a type of movement of the object or a change in size of the object.

The user input unit 200 may include, is not limited to, hardware components such as a keypad, a mouse, a touch pad, a touch screen, a trackball, a jog switch, etc. According to an embodiment, the user input unit 200 may be a touch screen that displays graphics user interfaces (GUIs) for selecting a frame having a defect associated with at least one of the type of movement of the object and a change in size of the object and receives a user touch input for selecting at least one from among the displayed GUIs. The configuration and operation of the user input unit 200 will be described in more detail below with reference to FIGS. 14 and 15.

The display 300 may display an ultrasound image obtained by the processor 100. According to an embodiment, the display 300 may display together a B mode ultrasound image, a CEUS image, a TIC, and a fitting curve. In one embodiment, the display 300 may display a difference value curve representing a difference between the TIC and the fitting curve for each ultrasound image frame and a threshold curve representing a threshold value for each ultrasound image frame. The display 300 may display a selected frame based on a user input received by the user input unit 200 for selecting a defective frame. According to an embodiment, the display 300 may display a position of a frame of an ultrasound image related to movement of the object and a change in size of the object in such a manner as to overlap the TIC.

In examination using a CEUS image, a frame of an ultrasound image captured when an object such as a tumor deviates outside an ROI, when a periodic movement occurs, when a size of the object changes, or when an ultrasound probe is not in contact with the object may act as a frame having a defect that may degrade the accuracy of the examination. According to an embodiment, the ultrasound diagnosis apparatus 1000 may analyze, based on a difference between a TIC and a fitting curve for an ultrasound image in an ROI, the type of movement of an object and a change in size of the object which cause defects, and provide a UI configured to select a defective frame based on an analysis result. Thus, the time required for a user to directly find and delete a defective frame may be shortened, and efficiency and reliability in analysis of an ultrasound image may be increased.

Since the ultrasound image processor 110, the ultrasound image analyzer 120, the user input unit 200, and the display 300 to be described below respectively correspond to the ultrasound image processor 110, the ultrasound image analyzer 120, the user input unit 200, and the display 300 described with reference to FIG. 1, detailed descriptions thereof will be omitted below.

Figure 2A:
FIG. 2A illustrates a graph showing a change in image signal values for each frame of an ultrasound image with respect to an object.

FIG. 2A illustrates a graph showing a change in image signal values for each frame of an ultrasound image with respect to an object;

Referring to FIG. 2A, the graph has a frame F of an ultrasound image on an X-axis and an image signal value for the ultrasound image on a Y-axis. In detail, successive frames of an ultrasound image generated by the ultrasound image processor 110 may be shown on the X-axis of the graph, and an average of image signal values, e.g., intensity values, of pixels in each of the successive frames may be shown on the Y-axis. The graph shown in FIG. 2A may be a bar graph showing a change in an average of intensity values for each of the successive frames. As shown in FIG. 2A, the intensity values for each ultrasound image frame gradually increases in proportion to the amount of contrast medium administered.

Figure 2B:
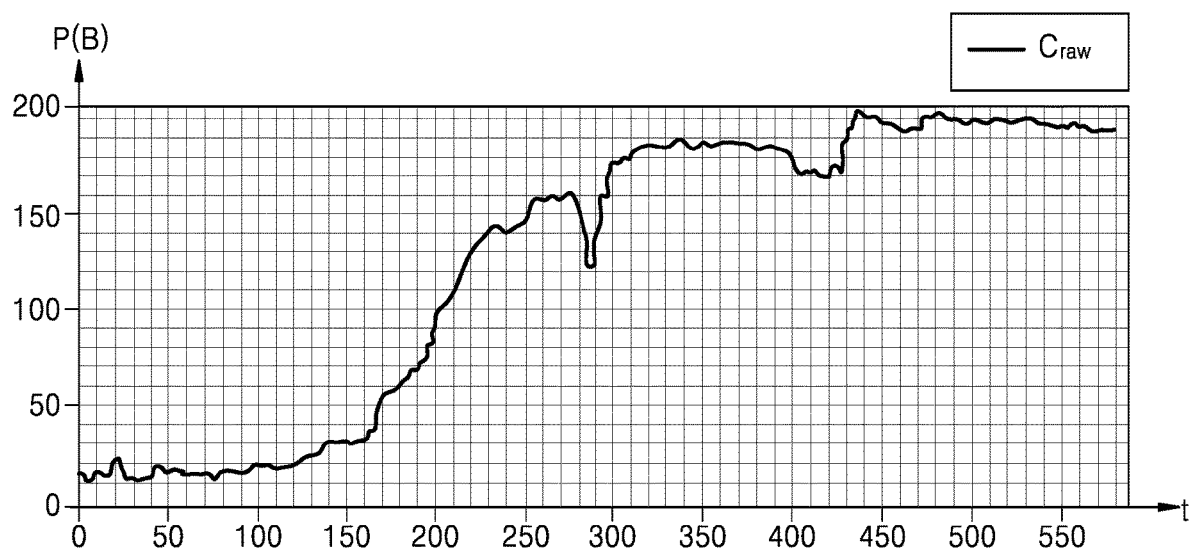
FIG. 2B illustrates a time intensity curve (TIC) of an ultrasound image of an object.
Figure 2C:
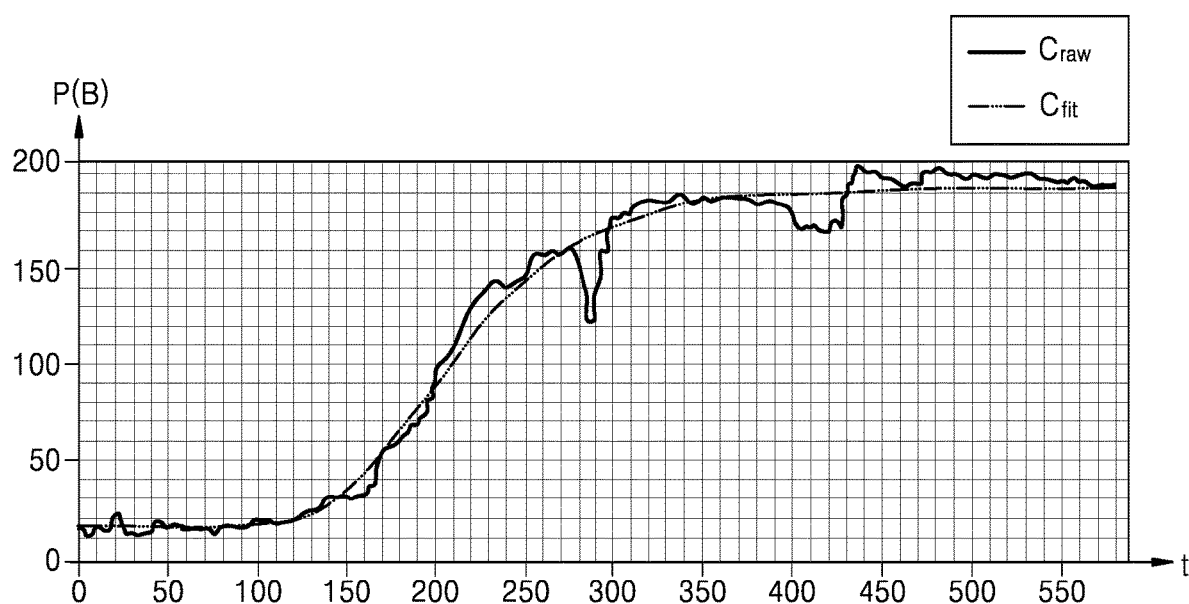
FIG. 2C illustrates the TIC and a fitting curve representing a tendency of the TIC.

FIG. 2B illustrates a TIC $C_{raw}$ of an ultrasound image of an object, and FIG. 2C illustrates the TIC $C_{raw}$ and a fitting curve $C_{fit}$ representing the tendency of the TIC $C_{raw}$.

Referring to FIG. 2B, the TIC $C_{raw}$ has time t on an X-axis and an average of intensity values for each of successive frames of an ultrasound image on a Y-axis. In detail, the time t is shown on the X-axis of the TIC $C_{raw}$ and represents the time during which the successive frames of the ultrasound image generated by the ultrasound image processor 110 are arranged at a particular sampling interval (frames per second (FPS)). An average of intensity values of pixels in each ultrasound image frame with respect to the object in an ROI is shown on the Y-axis. According to an embodiment, the TIC $C_{raw}$ may be displayed on the display 300.

Referring to FIG. 2C, a fitting curve $C_{fit}$ may be shown on a graph together with a TIC $C_{raw}$. The fitting curve $C_{fit}$ may be a graph showing the tendency of the TIC $C_{raw}$ based on a predefined mathematical model. According to an embodiment, the predefined mathematical model may include at least one of a polynomial model, exponential rise, gamma variant, and a sigmoidal model. In one embodiment, the TIC $C_{raw}$ and the fitting curve $C_{fit}$ may be displayed on the display 300.

Figure 2D:
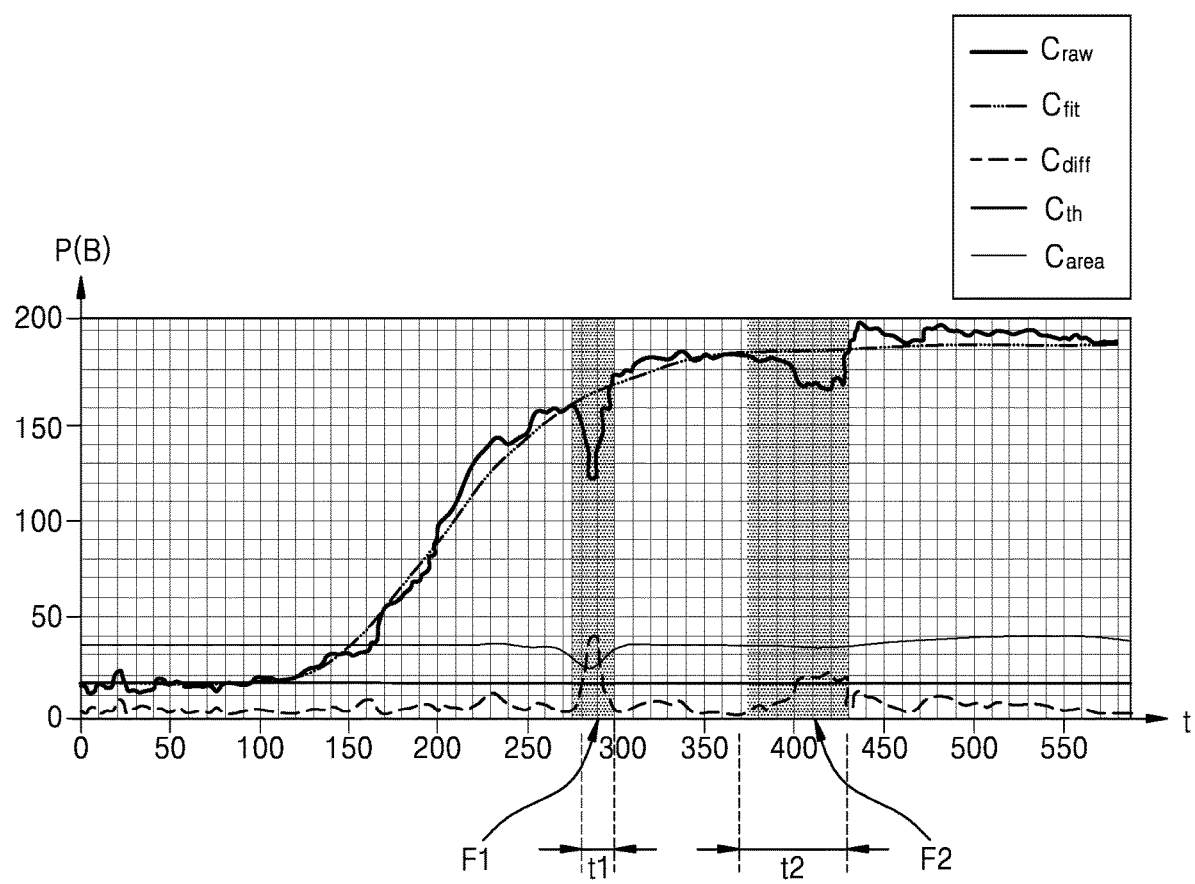
FIG. 2D illustrates a TIC of an ultrasound image of an object, a fitting curve, a difference value curve representing a difference value between the TIC and the fitting curve, a threshold curve, and a time area curve quantitatively representing a size of the object over time.

FIG. 2D illustrates a TIC $C_{raw}$ of an ultrasound image with respect to an object included in an ROI, a fitting curve $C_{fit}$, a difference value curve $C_{diff}$ representing a difference between the TIC $C_{raw}$ and the fitting curve $C_{fit}$, a threshold curve $C_{th}$, and a time area curve (TAC) $C_{area}$ quantitatively representing a size of the object over time. In one embodiment, the TIC $C_{raw}$, the fitting curve $C_{fit}$, the difference value curve $C_{diff}$, the threshold curve $C_{th}$, and the TAC $C_{area}$ may be displayed on the display 300.

A difference value curve $C_{diff}$ is a graph showing a difference between a TIC $C_{raw}$ of an ultrasound image with respect to an object included in an ROI and a fitting curve $C_{fit}$ for each ultrasound image frame. A threshold curve $C_{th}$ is a graph showing a threshold value for a difference for each ultrasound image frame. The threshold value may be calculated by using a preset calculation method. In one embodiment, the threshold value may be calculated as the sum of an average of differences for each ultrasound image frame and a standard deviation for the differences. In another embodiment, the threshold value may be calculated as the sum of a value that is twice the standard deviation for the differences and the average of the differences. According to an embodiment, the difference value curve $C_{diff}$ and the threshold value $C_{th}$ may be generated by the ultrasound image processor 110.

A TAC $C_{area}$ is a graph showing numerical values into which a size of an object included in an ROI is converted for each frame of an ultrasound image with respect to the object. In one embodiment, the ultrasound image processor 110 may acquire a TAC $C_{area}$ by using a tracking technique for tracking an edge of an object such as a tumor. Since the tracking technique is known to those of ordinary skill in the art, a detailed description thereof will be omitted here.

Referring to FIG. 2D, a frame F1 at which a difference between a TIC $C_{raw}$ and a fitting curve exceeds a threshold value may be included in a first time period t1. It can be seen on the TAC $C_{area}$ that a size of the object has decreased during the first time period t1. The ultrasound image analyzer 120 may determine that a size of the object included in an ROI has changed during the first time period t1 and that the frame F1 of the ultrasound image included in the first time period t1 contains information about a defect. Referring to the difference value curve $C_{diff}$ for a second time period t2, it can be seen that a difference between the TIC $C_{raw}$ and the fitting curve $C_{fit}$ exceeds a value on the threshold curve $C_{th}$. Furthermore, a TAC $C_{area}$ does not change and remains constant during the second time period t2. In this case, the ultrasound image analyzer 120 may determine that the object has deviated outside the ROI during the second time period t2 and that a frame F2 of the ultrasound image included in the second time period t2 contains information about a defect.

Figure 3:
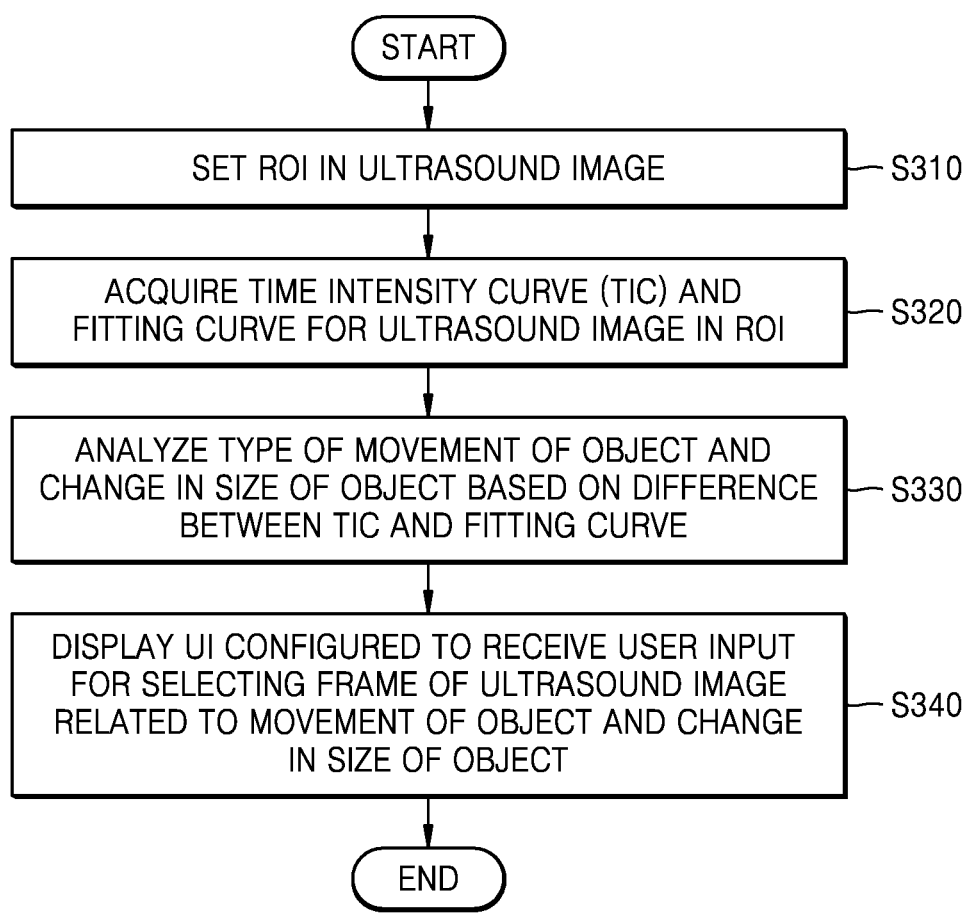
FIG. 3 is a flowchart of a method of analyzing an ultrasound image according to an embodiment.

FIG. 3 is a flowchart of a method of analyzing an ultrasound image according to an embodiment.

The ultrasound diagnosis apparatus 1000 sets an ROI in an ultrasound image (S310). According to an embodiment, the ultrasound image processor 110 may set an ROI in an ultrasound image obtained by the ultrasound transceiver. The ultrasound image processor 110 may set an ROI in an object depicted in an ultrasound image based on a user input received from the user input unit 200. However, embodiments are not limited thereto, and the ultrasound image processor 110 may recognize an object such as a tumor and automatically set an ROI along an edge of the tumor.

The ultrasound diagnosis apparatus 1000 acquires a TIC and a fitting curve for the ultrasound image within the ROI (S320). In one embodiment, the ultrasound image processor 110 may calculate an average of image signal values, e.g., intensity values, for each ultrasound image frame within the set ROI and generate a TIC that is a graph showing the calculated average of intensity values for frames of the ultrasound image. The ultrasound image processor 110 may also generate a fitting curve representing the tendency of the TIC. According to an embodiment, the ultrasound image processor 110 may analyze the tendency of the TIC based on a predefined mathematical model and generate a fitting curve that is a graph showing values corresponding to the analyzed tendency for a frame of an ultrasound image.

The ultrasound diagnosis apparatus 1000 analyzes the type of movement of an object and a change in size of the object based on a difference between the TIC and the fitting curve (S330). In one embodiment, the ultrasound image analyzer 120 may analyze, based on a difference value curve representing a difference between the TIC and the fitting curve for each ultrasound image frame, whether the object deviates outside the ROI, whether the object moves periodically, whether a size of the object changes, and whether an ultrasound probe is not in contact with the object. According to an embodiment, the ultrasound image analyzer 120 may determine whether the difference between the TIC and fitting curve exceeds a threshold value and determine a defective frame from among frames of the ultrasound image.

The ultrasound diagnosis apparatus 1000 displays a UI configured to receive a user input for selecting a frame of the ultrasound image related to the type of the movement of the object or the change in size of the object (S340). The user input unit 200 may receive a user input for selecting a frame of the ultrasound image related to the type of the movement of the object or the change in size of the object. According to an embodiment, the user input unit 200 may display a UI configured to select a frame of the ultrasound image related to at least one of the type of the movement of the object or the change in size of the object.

Figure 4:
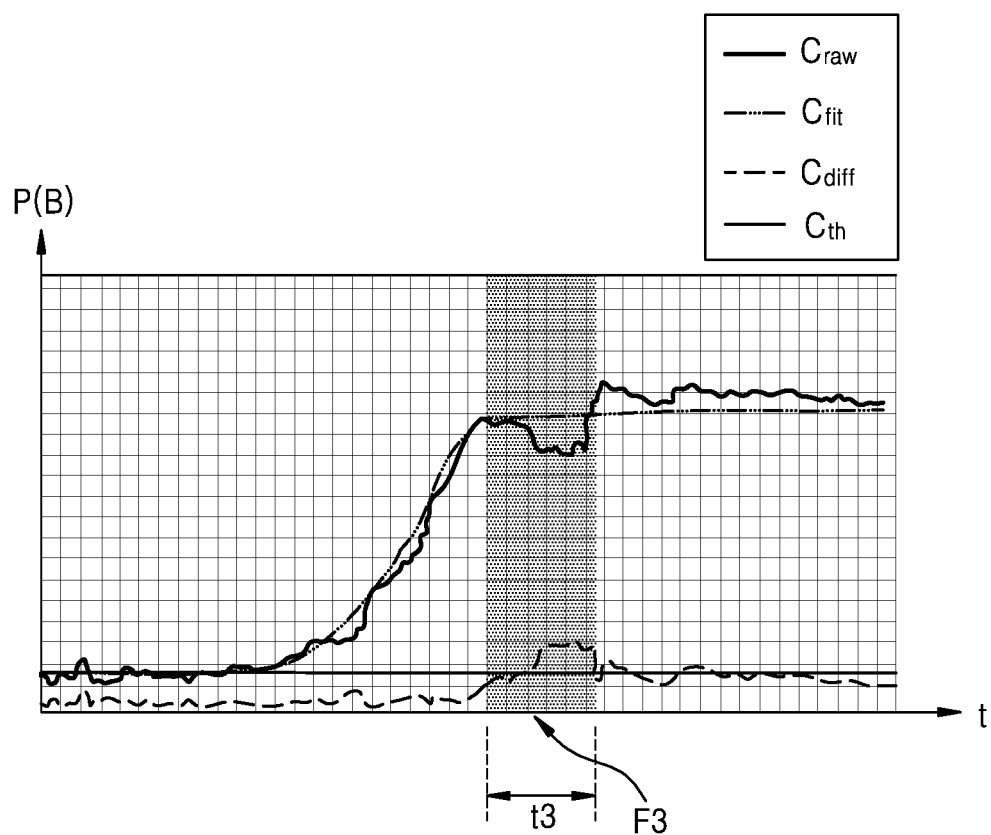
FIG. 4 illustrates a TIC and a fitting curve for an ultrasound image of an object according to an embodiment.

FIG. 4 illustrates a TIC $C_{raw}$ and a fitting curve $C_{fit}$ for an ultrasound image of an object according to an embodiment.

Referring to FIG. 4, an X-axis represents time during which frames of an ultrasound image are arranged at a particular sampling interval (FPS), and a Y-axis represents a magnitude of image signal values for each ultrasound image frame. The TIC $C_{raw}$ representing an average of intensity values for each ultrasound image frame and a fitting curve $C_{fit}$ representing the tendency of the TIC $C_{raw}$ based on a predefined mathematical model is shown in FIG. 4. Furthermore, a difference value curve $C_{diff}$ representing a difference between the TIC $C_{raw}$ and the fitting curve $C_{fit}$ for each ultrasound image frame and a threshold curve $C_{th}$ representing a threshold value for the difference is shown together in FIG. 4. In one embodiment, the TIC $C_{raw}$, the fitting curve $C_{fit}$, the difference value curve $C_{diff}$, and the threshold curve $C_{th}$ may be displayed together on the display 300 to allow the user to easily analyze the ultrasound image based thereon.

As shown in FIG. 4, a difference between the TIC $C_{raw}$ and the fitting curve $C_{fit}$ for a third time period t3, i.e., a value on the difference value curve $C_{diff}$, exceeds a corresponding value on the threshold curve $C_{th}$. In one embodiment, the ultrasound image analyzer 120 may determine that an object has deviated outside an ROI during the third time period t3. In other words, the ultrasound image analyzer 120 may determine from analysis that intensity values of an ultrasound image frame differ greatly from those of other adjacent ultrasound image frames, and determine the ultrasound image frame F3 as being a defective frame in which the object has deviated outside the ROI. A method, performed by the ultrasound image analyzer 120, of analyzing a deviation of an object away from an ROI will now be described in more detail with reference to FIG. 5.

Figure 5:
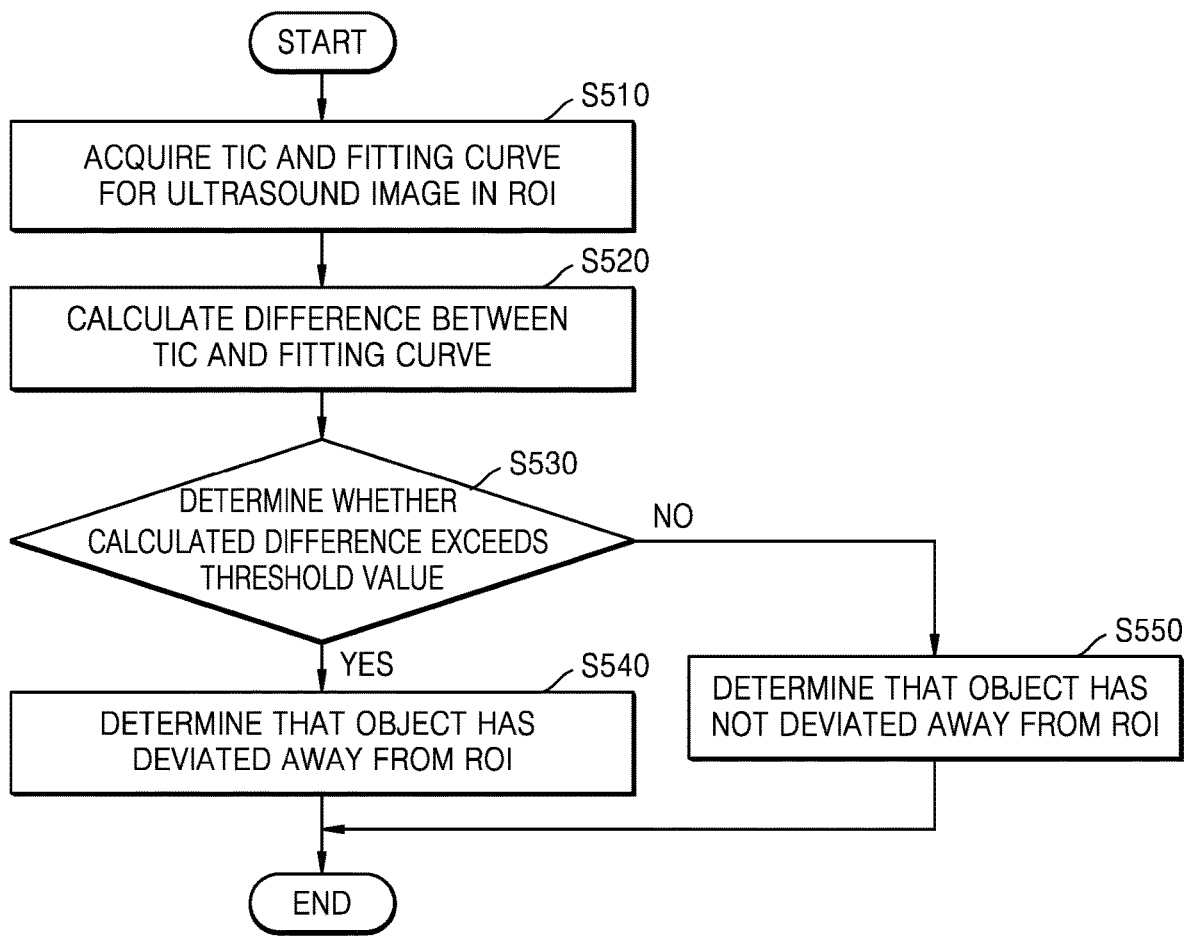
FIG. 5 is a flowchart of a method of analyzing a defect in an ultrasound image by determining whether an object has deviated away from a region of interest (ROI), according to an embodiment.

FIG. 5 is a flowchart of a method of analyzing a defect in an ultrasound image by determining whether an object has deviated away from an ROI, according to an embodiment.

The ultrasound diagnosis apparatus 1000 acquires a TIC and a fitting curve for an ultrasound image within an ROI (S510). Since operations of setting an ROI in an ultrasound image and generating a TIC and a fitting curve based on intensity values of the ultrasound image within the ROI, which are performed by the ultrasound image processor 110, correspond to operations S310 and S320 described with reference to FIG. 3, the same descriptions that are already provided above with respect to FIG. 3 will be omitted below.

The ultrasound diagnosis apparatus 1000 calculates a difference between the TIC and the fitting curve (S520). In one embodiment, the ultrasound image analyzer 120 may calculate a difference between the TIC and the fitting curve for each ultrasound image frame and generate a difference value curve representing the calculated difference therebetween.

The ultrasound diagnosis apparatus 1000 determines whether the calculated difference exceeds a threshold value (S530). According to an embodiment, the ultrasound image analyzer 120 may compare a difference value curve for each ultrasound image frame with a preset threshold curve to determine a frame in which the difference exceeds the threshold value. In this case, the threshold value may be obtained based on an average value obtained by dividing the sum of differences for frames of the ultrasound image by the number of frames and a standard deviation for the differences.

When it is determined that the calculated difference exceeds the threshold value for a frame of the ultrasound image, the ultrasound diagnosis apparatus 1000 determines that the frame has been captured when the object deviates away from the ROI (S540). According to an embodiment, when a difference value curve for a frame of the ultrasound image is located above a threshold curve, the ultrasound image analyzer 120 may determine that the object has deviated away from the ROI since there is a large difference in intensity values for the ultrasound image within the ROI and thus determine the frame as a defective frame.

When it is determined that the calculated difference does not exceed the threshold value for a frame of the ultrasound image, the ultrasound diagnosis apparatus 1000 determines that the frame has been captured when the object is located within the ROI (S550). The ultrasound diagnosis apparatus 1000. In one embodiment, the ultrasound image analyzer 120 may determine the frame of the ultrasound image at which the calculated difference does not exceed the threshold value as a defect-free frame.

Figure 6A:
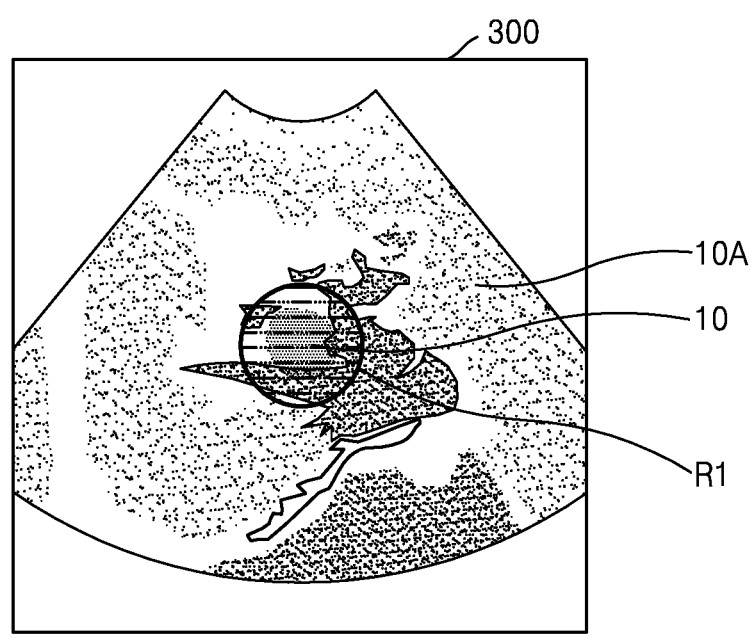
FIGS. 6A through 6C are diagrams for explaining setting of an ROI and an additional ROI in an ultrasound image according to embodiments.
Figure 6B:
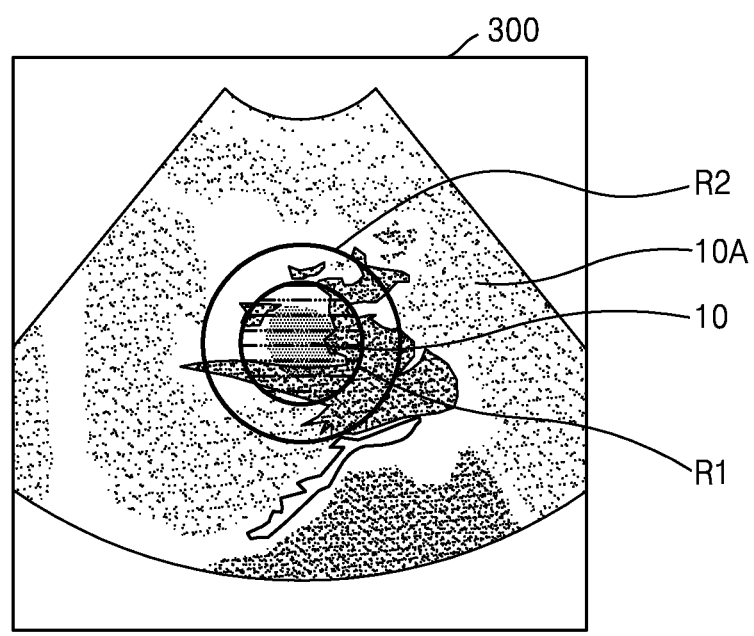
Figure 6C:
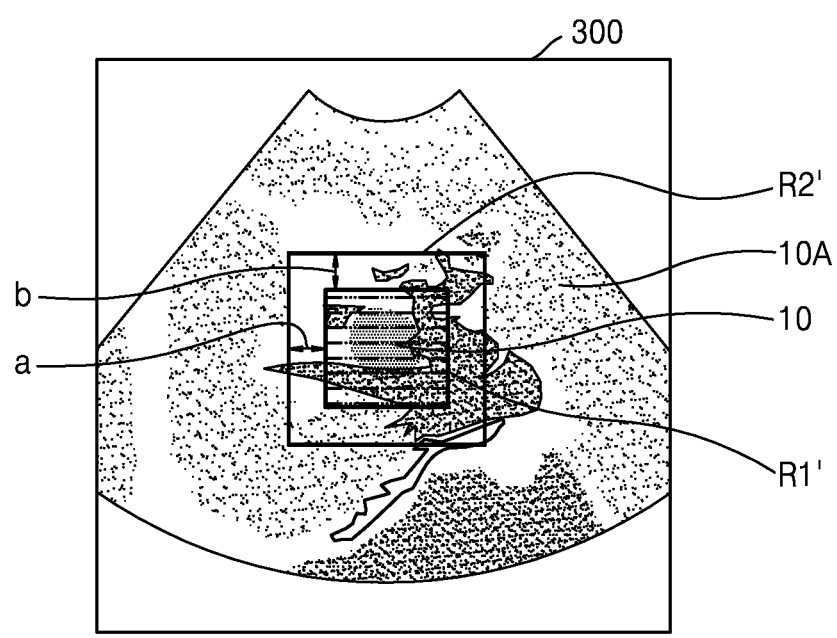

FIGS. 6A through 6C are diagrams for explaining setting of ROIs R1 and R2 in an ultrasound image 10A according to embodiments.

Referring to FIG. 6A, the ultrasound image 10A generated by the ultrasound image processor 110 is displayed on the display 300. The ultrasound image processor 110 may set the ROI R1 in the ultrasound image 10A. In one embodiment, the user input unit 200 may receive a user input for setting the ROI R1 in the ultrasound image 10A, and the ultrasound image processor 110 may set the ROI R1 in the ultrasound image 10A based on the user input. A position, a shape, and a size of the ROI R1 may be arbitrarily changed according to the user input.

According to an embodiment, the ultrasound image processor 110 may detect an object 10 such as a tumor by using a tracking function and set the ROI R1 along an edge of the detected tumor. In one embodiment, the ultrasound image processor 110 may set a plurality of ROIs R1 in the ultrasound image 10A.

Referring to FIG. 6B, the ultrasound image processor 110 may set an additional ROI R2 in the ultrasound image 10A. The additional ROI R2 may be larger than the preset ROI R1 and include the ROI R1. In one embodiment, the ultrasound image processor 110 may automatically set the additional ROI R2 to be a region including the initially set ROI R1. The additional ROI R2 may be wider than the ROI R1 by a particular amount. When the ROI R1 and the additional ROI R2 have a circular shape as shown in FIG. 6B, the additional ROI R2 may be set to also have a circular shape with a diameter greater than that of the ROI R2.

In another embodiment, the user input unit 200 may receive a user input for setting the additional ROI R2 in the ultrasound image 10A, and the ultrasound image processor 110 may set the additional ROI R2 with respect to the object 10 in the ultrasound image 10A based on the user input. The additional ROI R2 may be set to be a region including the ROI R1, and may include the object 10 to be observed by a user.

Referring to FIG. 6C, the ultrasound image processor 110 may set an ROI R1' and an additional ROI R2' to have a quadrilateral shape. The ultrasound image processor 110 may automatically set the additional ROI R2' obtained by expanding the initially set ROI R1' by a particular size. In one embodiment, the ultrasound image processor 110 may automatically set the additional ROI R2' to have a width that is greater than that of the ROI R1' by a first size a and a length that is greater than that of the ROI R1' by a second size b.

In the embodiments shown in FIGS. 6B and 6C, the ultrasound image analyzer 120 may generate a TIC for each ultrasound image frame 10A included in the additional ROI R2 (R2'), and analyze whether the object 10 such as a tumor has changed by analyzing a change in intensity values for the ultrasound image 10A with respect to the additional ROI R2 (R2') as will be described in more detail with reference to FIG. 7.

Figure 7:
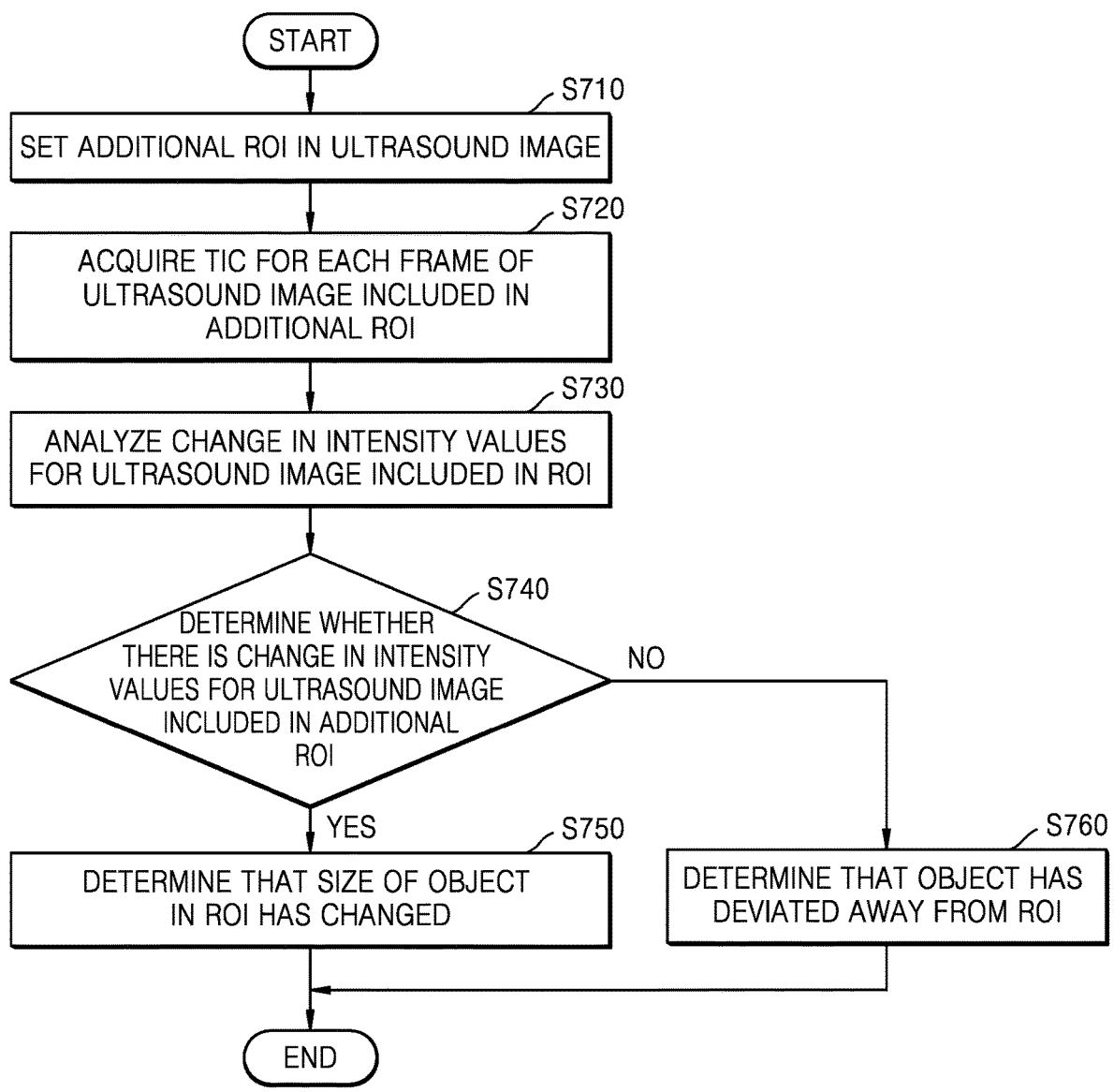
FIG. 7 is a flowchart of a method of analyzing a defective ultrasound image based on analysis of a motion of an object or a change in size of the object, according to an embodiment.

FIG. 7 is a flowchart of a method of analyzing a defective ultrasound image based on the analysis of movement of an object or a change in size of the object, according to an embodiment.

The ultrasound diagnosis apparatus 1000 sets an additional ROI in an ultrasound image (S710). In one embodiment, the user input unit 200 may receive a user input for setting an additional ROI that is larger than and includes an ROI, and the ultrasound image processor 110 may set the additional ROI based on the user input.

The ultrasound diagnosis apparatus 1000 acquires a TIC for each frame of an ultrasound image included in the additional ROI (S720). According to an embodiment, the ultrasound image processor 110 may calculate an average of intensity values for each ultrasound image frame included in the additional ROI by converting the intensity values into numerical values and generate a TIC regarding the additional ROI based on the calculated average of intensity values. Since an operation of generating a TIC corresponds to operation S320 described with reference to FIG. 3 except for a size of the ROI, the same descriptions already provided with respect to FIG. 3 will be omitted below.

The ultrasound diagnosis apparatus 1000 determines whether there is a change in intensity values for the ultrasound image with respect to an object included in an ROI (S730). According to an embodiment, the ultrasound image analyzer 120 may generate a TIC representing an average of intensity values for each ultrasound image frame with respect to an object included in the ROI and analyze a change in intensity values for the ultrasound image within the ROI based on the TIC.

The ultrasound diagnosis apparatus 1000 determines whether there is a change in intensity values for the ultrasound image with respect to the object included in the additional ROI (S740). According to an embodiment, the ultrasound image analyzer 120 may generate a TIC for each ultrasound image frame within the additional ROI and analyze a change in intensity values for a frame of the ultrasound image included in the additional ROI based on the TIC for the additional ROI.

When it is determined that there is a change in the intensity values for the ultrasound image with respect to the object included in the additional ROI, the ultrasound diagnosis apparatus 1000 determines that a size of the object within the ROI has changed (S750). When it is determined that there is a change in the intensity values for the ultrasound image with respect to the object included in the ROI (S730) and that there is a change in the intensity values for the ultrasound image with respect to the object included in the additional ROI (S740), the ultrasound image analyzer 120 may determine that the size of the object within the ROI has changed. In one embodiment, an ultrasound frame captured when the size of the object changes may be a defective frame.

When the ultrasound diagnosis apparatus 1000 determines that there is no change in the intensity values for the ultrasound image with respect to the object included in the additional ROI but that there is a change in intensity values for a frame of the ultrasound image included in the ROI, the ultrasound diagnosis apparatus 1000 determines that the object has deviated away from the ROI (S760). When it is determined that there is a change in the intensity values for the ultrasound image with respect to the object included in the ROI (S730) but that there is no change in the intensity values for the ultrasound image with respect to the object included in the additional ROI (S740), the ultrasound image analyzer 120 may determine that the object has moved outside of the ROI. In one embodiment, an ultrasound frame captured when the object deviates outside the ROI may be a defective frame.

Figure 8:
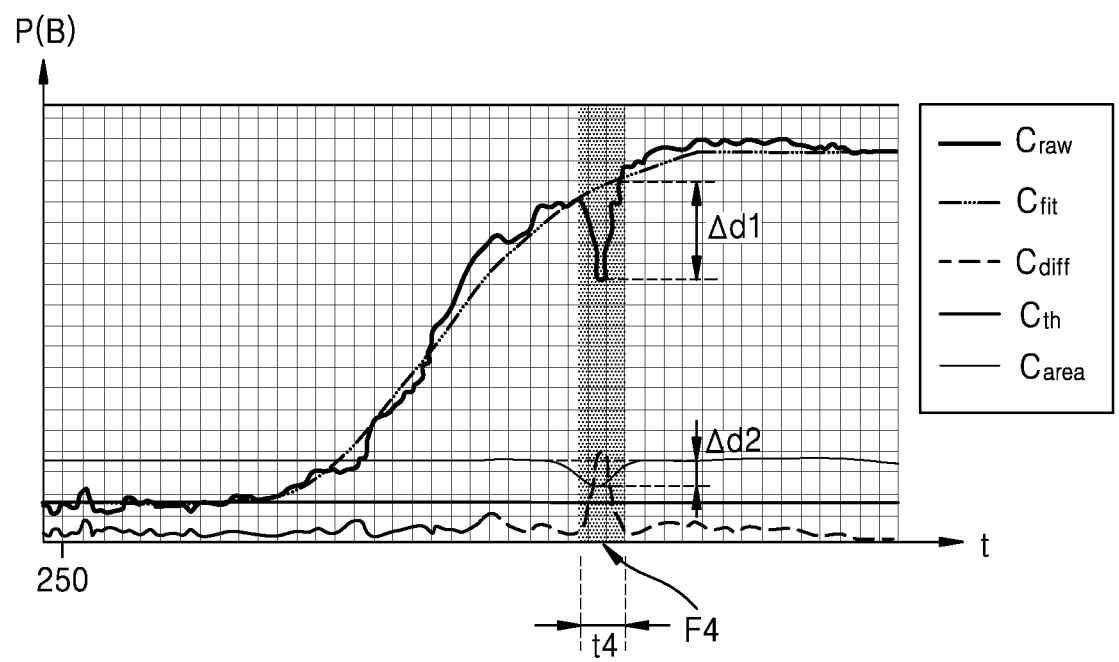
FIG. 8 illustrates a TIC, a fitting curve, a difference value curve, a threshold curve, and a time area curve for an ultrasound image of an object, according to an embodiment.

FIG. 8 illustrates a TIC $C_{raw}$, a fitting curve $C_{fit}$, a difference value curve $C_{diff}$, a threshold curve $C_{th}$, and a time area curve $C_{area}$ for an ultrasound image of an object, according to an embodiment. A TIC $C_{raw}$ representing an average of intensity values for each frame of an ultrasound image and a fitting curve $C_{fit}$ representing the tendency of the TIC $C_{raw}$ based on a predefined mathematical model may be shown in FIG. 8. Furthermore, a difference value curve $C_{diff}$ representing a difference between the TIC $C_{raw}$ and the fitting curve $C_{fit}$ for each ultrasound image frame, a threshold curve $C_{th}$ representing a threshold value for the difference, and a TAC $C_{area}$ representing a size of the object for each ultrasound image frame may be shown together in FIG. 8. In one embodiment, the TIC $C_{raw}$, the fitting curve $C_{fit}$, the difference value curve $C_{diff}$, the threshold curve $C_{th}$, and the TAC $C_{area}$ may be displayed together on the display 300 to allow the user to easily analyze the ultrasound image based thereon.

Referring to FIG. 8, a value on the difference value curve $C_{diff}$ exceeds a corresponding value on the threshold curve $C_{th}$ during a fourth time period t4. In one embodiment, a difference between the TIC $C_{raw}$ and the fitting curve $C_{fit}$ corresponding to a first size Δd1 may occur. Furthermore, the TAC $C_{area}$ may fluctuate and show a difference corresponding to a second size Δd2 during the fourth time period t4. The ultrasound image analyzer 120 may detect that a value on the difference value curve $C_{diff}$ exceeds a threshold value for an ultrasound image frame F4 in the fourth time period t4 and that the TAC $C_{area}$ has a value for the ultrasound image frame F4 that is less than a value for its adjacent frame. The ultrasound image analyzer 120 may analyze the ultrasound image frame F4 as a frame captured when the size of the object changes. In the embodiment shown in FIG. 8, the ultrasound image analyzer 120 may determine that the size of the object has decreased at the ultrasound image frame F4. A method of analyzing a change in size of an object will now be described in detail with reference to FIG. 9.

Figure 9:
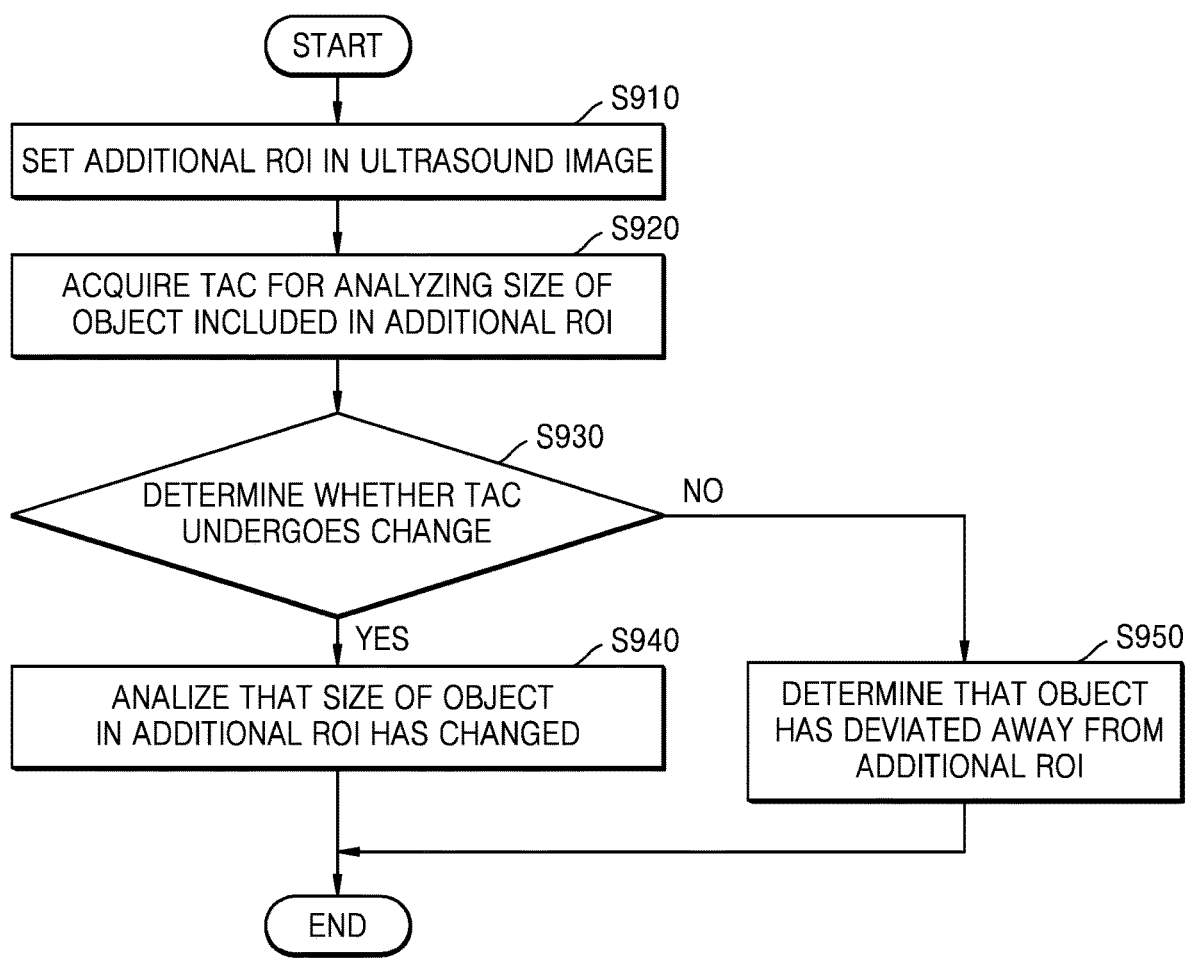
FIG. 9 is a flowchart of a method of analyzing a defective ultrasound image based on analysis of a change in size of an object, according to an embodiment.

FIG. 9 is a flowchart of a method of analyzing a defective ultrasound image based on the analysis of a change in size of an object, according to an embodiment.

The ultrasound diagnosis apparatus 1000 sets an additional ROI in an ultrasound image (S910). Since an operation of setting an additional ROI corresponds to operation S710 described with reference to FIG. 7, the same descriptions already provided with reference to FIG. 7 will be omitted here.

The ultrasound diagnosis apparatus 1000 acquires a TAC for analyzing a size of an object included in the additional ROI (S920). According to an embodiment, the ultrasound image processor 110 may generate a TAC as a graph showing numerical values into which a size of the object included in the ROI is converted for each ultrasound image frame. In one embodiment, the TAC may be obtained by using a tracking technique for tracking an edge of the object such as a tumor.

The ultrasound diagnosis apparatus 1000 determines whether the TAC undergoes a change (S930). The ultrasound image analyzer 120 may determine the degree of change in the TAC. According to an embodiment, when the TAC keeps a constant value across successive frames of an ultrasound image and undergoes a change to have a value exceeding the threshold value at a specific frame, the ultrasound image analyzer 120 may detect the specific frame. According to an embodiment, the ultrasound image analyzer may analyze a difference between a TIC and a fitting curve to detect a frame of an ultrasound image at which the difference exceeds a predetermined threshold value and subsequently analyze a change in the degree of change in a TAC. However, embodiments are not limited thereto, and the ultrasound image analyzer 120 may simultaneously perform analyses to determine a difference between a TIC and a fitting curve and the degree of change in a TAC.

The ultrasound diagnosis apparatus 1000 analyzes a change in the TAC and, when the change occurs in the TAC, determines that the size of the object within the additional ROI has changed (S940). According to an embodiment, when the TAC keeps a constant value and undergoes a change to have a value exceeding the threshold value at a specific frame, the ultrasound image analyzer 120 may analyze the change to determine that the size of the object has changed at the specific frame. The ultrasound image analyzer 120 may define the specific frame as a defective frame.

When the ultrasound diagnosis apparatus 1000 determines that the TAC undergoes no change, the ultrasound diagnosis apparatus 1000 determines that the object has deviated away from the additional ROI (S950). When it is determined that the TAC undergoes no change in the additional ROI, and in particular, at a frame of an ultrasound image for which a difference between a TIC and a fitting curve exceeds a threshold value, the ultrasound image analyzer 120 may determine that the object has simply deviated away from the additional ROI. In other words, the ultrasound image analyzer 120 may determine that the size of the object does not change and the object has deviated away from the ROI at the frame of the ultrasound image. The ultrasound image analyzer 120 may define the frame of the ultrasound image in which the object is determined to deviate away from the ROI as a defective frame.

Figure 10:
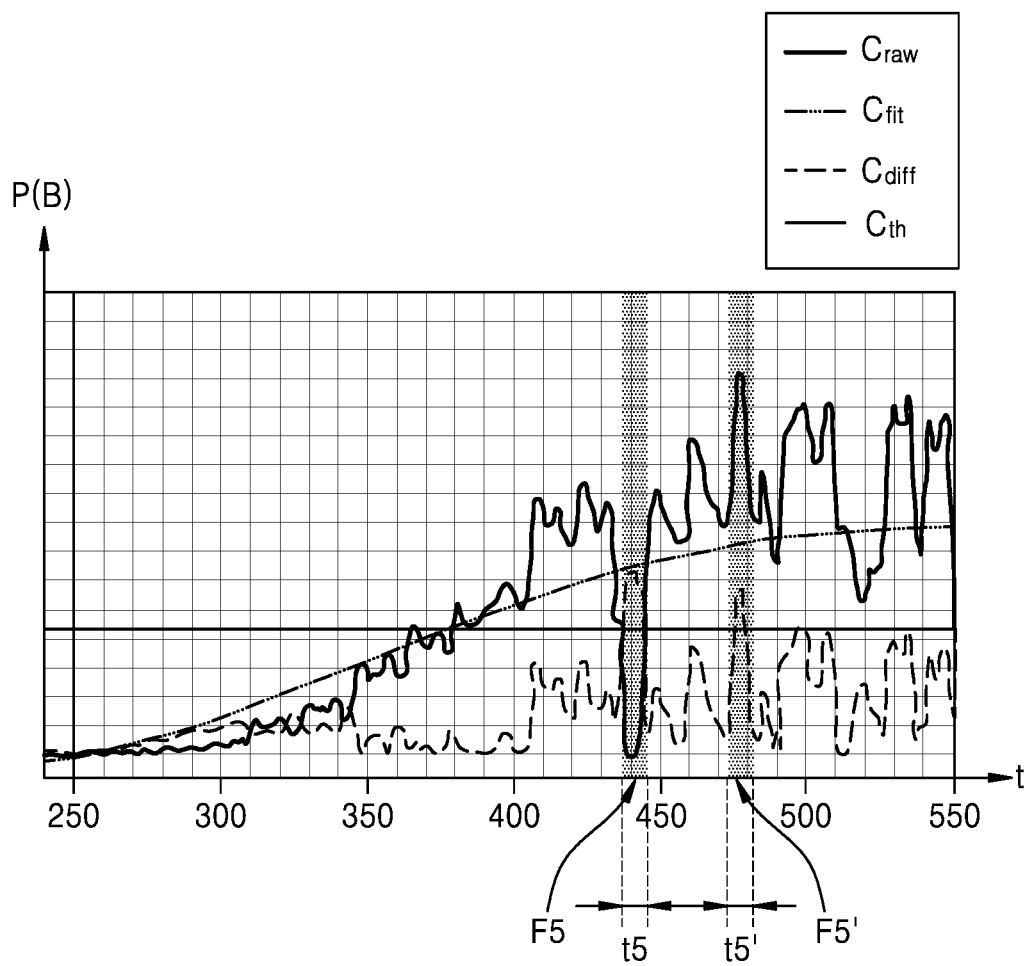
FIG. 10 illustrates a TIC, a fitting curve, a difference value curve, and a threshold curve for an ultrasound image of an object, according to an embodiment.

FIG. 10 illustrates a TIC $C_{raw}$, a fitting curve $C_{fit}$, a difference value curve $C_{diff}$, and a threshold curve $C_{th}$ for an ultrasound image for an object, according to an embodiment.

A TIC $C_{raw}$ representing an average of intensity values for each frame of an ultrasound image and a fitting curve $C_{fit}$ representing the tendency of the TIC $C_{raw}$ based on a predefined mathematical model may be shown in FIG. 10. Furthermore, a difference value curve $C_{diff}$ representing a difference between the TIC $C_{raw}$ and the fitting curve $C_{fit}$ for each ultrasound image frame and a threshold curve $C_{th}$ representing a threshold value for the difference may be shown together in FIG. 10. In one embodiment, the TIC $C_{raw}$, the fitting curve $C_{fit}$, the difference value curve $C_{diff}$, and the threshold curve $C_{th}$ may be displayed together on the display 300.

In general, the TIC $C_{raw}$ shows values increasing over time according to a certain tendency, but may intermittently indicate a value of 0 against the tendency during the fifth time period t5 and the fifth' time period t5'. The ultrasound image analyzer 120 may detect a frame at which the TIC has a value of 0 from among frames of the ultrasound image. According to an embodiment, the ultrasound image analyzer 120 may analyze a frame of an ultrasound image at which the TIC has a value of 0 and determine the frame as a frame captured when an ultrasound probe is not in contact with an object. In examination using a CEUS image, an ultrasound probe may not be in contact with the object due to movement of a user holding the ultrasound probe or movement of an examinee. When an ultrasound image is captured with the ultrasound probe not being in contact with the object, an ultrasound image of an object may not obtained, and the captured ultrasound image may be a defective image not suitable for the examination. In one embodiment, by analyzing a TIC $C_{raw}$ and defining a frame of an ultrasound image having an intensity value of 0 as a defective frame via the ultrasound image analyzer 120, it is possible to shorten the time required for examination using the ultrasound image and increase reliability in the examination.

Figure 11:
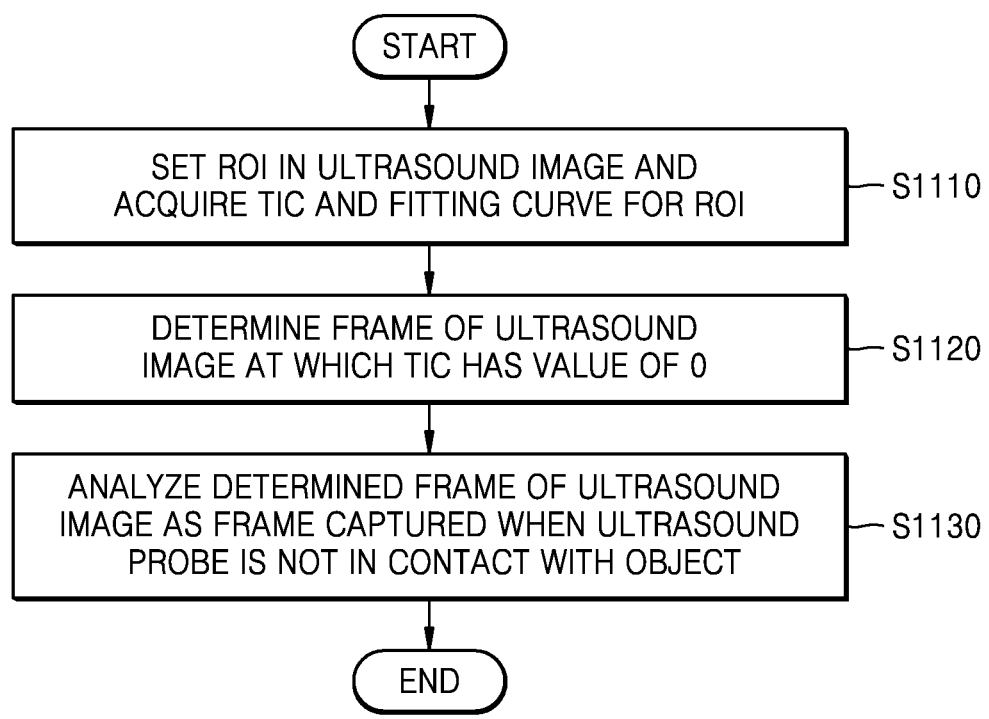
FIG. 11 is a flowchart of a method of analyzing a defective ultrasound image by determining whether or not an ultrasound probe is in contact with an object, according to an embodiment.

FIG. 11 is a flowchart of a method of analyzing a defective ultrasound image by determining whether an ultrasound probe is not in contact with an object.

The ultrasound diagnosis apparatus 1000 sets an ROI in an ultrasound image and acquires a TIC and a fitting curve for the ROI (S1110). Since operations of setting an ROI and generating a TIC and a fitting curve respectively correspond to operations S310 and S320 described with reference to FIG. 3, the same descriptions already provided with respect to FIG. 3 will be omitted below.

The ultrasound diagnosis apparatus 1000 determines a frame of the ultrasound image at which the TIC has a value of 0 (S1120). In one embodiment, the ultrasound image analyzer 120 may detect a frame of an ultrasound image having an intensity value of 0 against a tendency of a TIC $C_{raw}$.

The ultrasound diagnosis apparatus 1000 analyzes the determined frame of ultrasound image as a frame captured when an ultrasound probe is not in contact with the object (S1130). In one embodiment, the ultrasound image analyzer 120 may analyze a TIC and define a frame of an ultrasound image having an intensity value of 0 as a defective frame.

Figure 12:
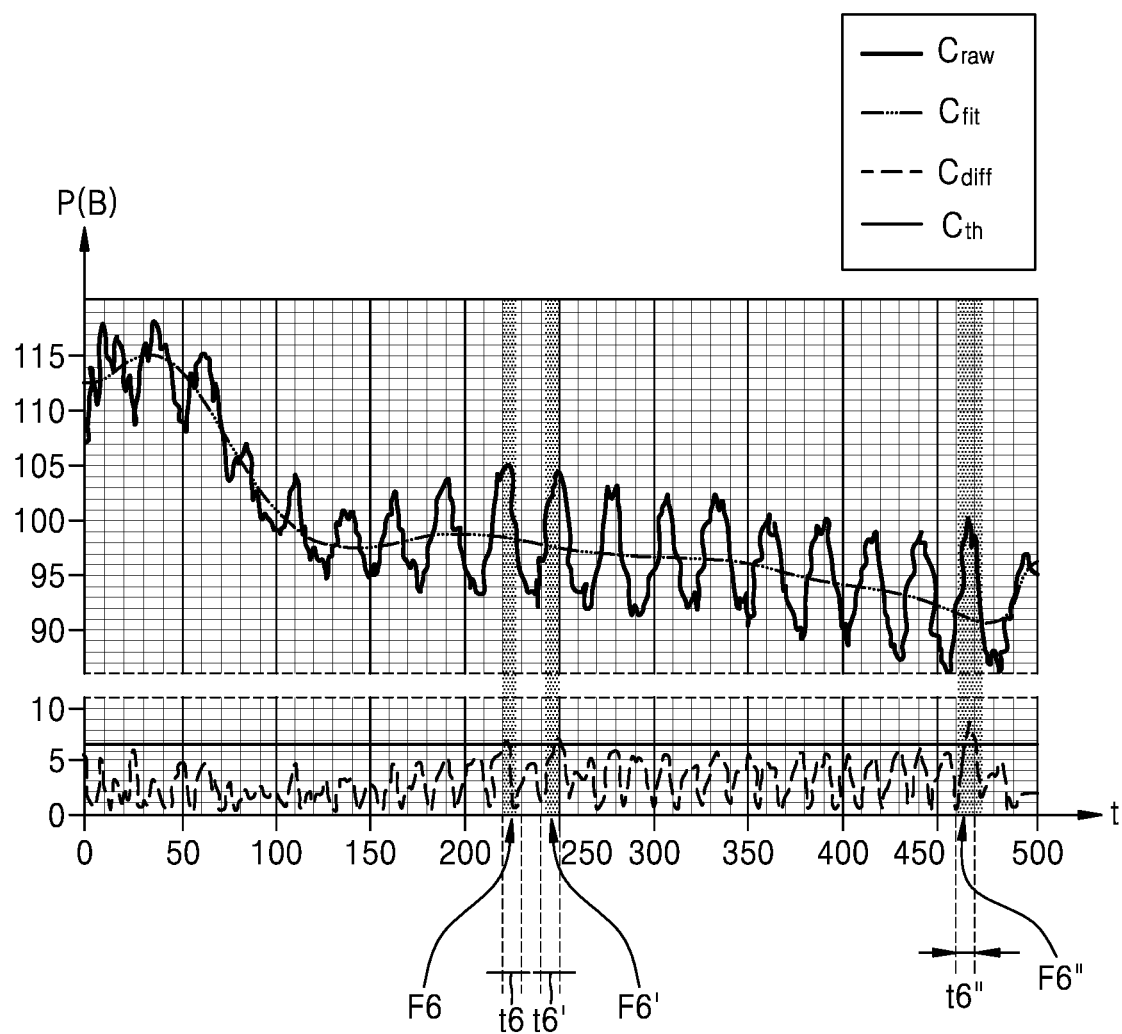
FIG. 12 illustrates a TIC, a fitting curve, a difference value curve, and a threshold curve for an ultrasound image of an object, according to an embodiment.

FIG. 12 illustrates a TIC $C_{raw}$, a fitting curve $C_{fit}$, a difference value curve $C_{diff}$, and a threshold curve $C_{th}$ for an ultrasound image for an object, according to an embodiment.

A TIC $C_{raw}$ representing an average of intensity values for each frame of an ultrasound image and a fitting curve $C_{fit}$ representing the tendency of the TIC $C_{raw}$ based on a predefined mathematical model may be shown in FIG. 12. Furthermore, a difference value curve $C_{diff}$ representing a difference between the TIC $C_{raw}$ and the fitting curve $C_{fit}$ for each ultrasound image frame and a threshold curve $C_{th}$ representing a threshold value for the difference may be shown together in FIG. 12. In one embodiment, the TIC $C_{raw}$, the fitting curve $C_{fit}$, the difference value curve $C_{diff}$, and the threshold curve $C_{th}$ may be displayed together on the display 300.

The TIC $C_{raw}$ shown in FIG. 12 does not show a certain tendency over time, i.e., with respect to successive frames of an ultrasound image but periodically changes. A difference between the fitting curve $C_{fit}$ representing the tendency of the TIC $C_{raw}$ and the TIC $C_{raw}$ does not also remain constant across successive frames of the ultrasound image but periodically changes. In the embodiment shown in FIG. 12, a difference between the TIC $C_{raw}$ and the fitting curve $C_{fit}$ may exceed a threshold value during a sixth time period t6, a sixth' time period t6' and a sixth" time period t6". According to an embodiment, the ultrasound image analyzer 120 may analyze whether a periodic movement of an object occurs by examining intensity values indicated in the TIC $C_{raw}$ that undergoes a periodic change in values and a periodic change in a difference value curve $C_{raw}$ $C_{diff}$. For example, when CEUS examination is performed after administration of contrast medium to an object, i.e., a tumor located near a hepatic artery or the heart, the object (or tumor) may periodically move due to a periodic movement of the hepatic artery or beating of the heart. Since such a periodic movement of the object causes a periodic change in a TIC $C_{raw}$, the ultrasound image analyzer 120 may analyze the periodic change in the TIC $C_{raw}$ and detect the periodic movement of the object based on the periodic change in the TIC $C_{raw}$. In this case, the periodic movement of the object near the hepatic artery or the heart is normal, and a frame of the ultrasound image at which it is determined that the periodic movement of the object occurs does not directly affect the result of the CEUS examination. Thus, the ultrasound image analyzer 120 may not define the frame of the ultrasound image as a defective frame.

Figure 13:
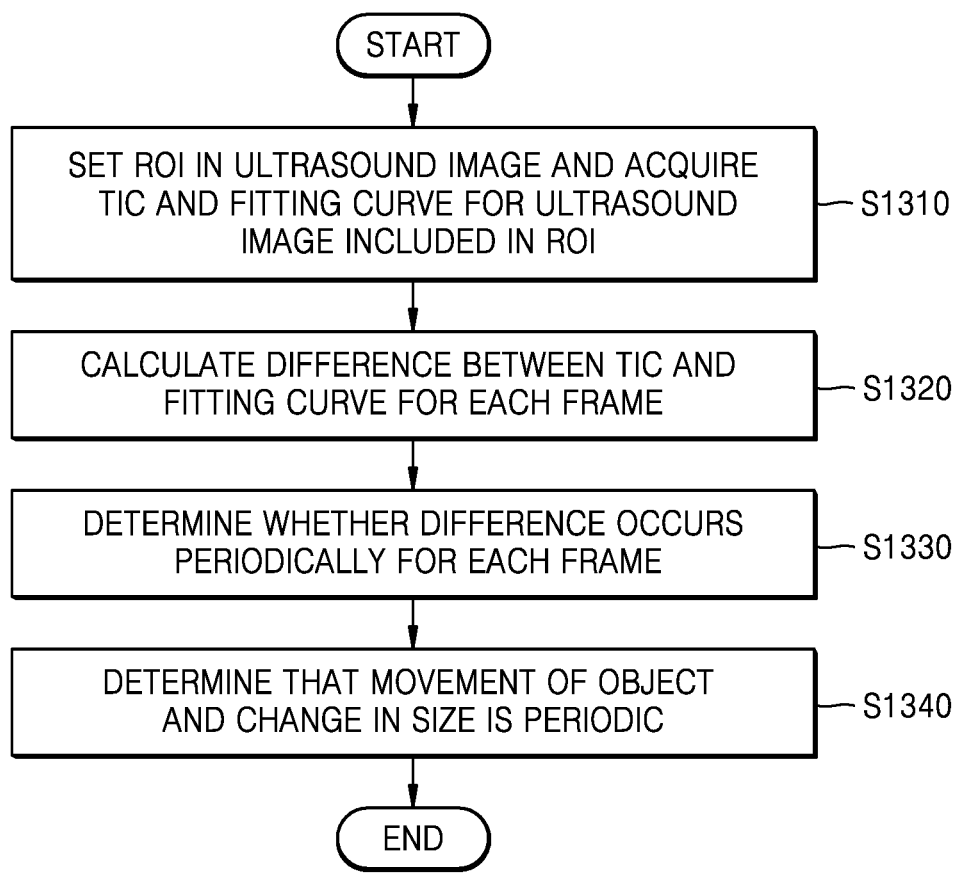
FIG. 13 is a flowchart of a method of determining whether a motion of an object or a change in size of the object occurs periodically, according to an embodiment.

FIG. 13 is a flowchart of a method of determining whether movement of an object or a change in size of the object occurs periodically, according to an embodiment.

The ultrasound diagnosis apparatus 1000 sets an ROI in an ultrasound image and acquires a TIC and a fitting curve for an ultrasound image with respect to an object included in the ROI (S1310). Since operations of setting an ROI and generating a TIC and a fitting curve respectively correspond to operations S310 and S320 described with reference to FIG. 3, the same descriptions already provided with respect to FIG. 3 will be omitted below.

The ultrasound diagnosis apparatus 1000 calculates a difference between the TIC and the fitting curve for each ultrasound image frame (S1320). In one embodiment, the ultrasound image analyzer 120 may generate a difference value curve representing a difference between the TIC and the fitting curve for each ultrasound image frame.

The ultrasound diagnosis apparatus 1000 determines whether the difference occurs periodically for each ultrasound image frame (S1330). According to an embodiment, the ultrasound image analyzer 120 may determine whether the difference between the TIC and the fitting curve periodically exceeds a threshold value. Furthermore, the ultrasound image analyzer 120 may determine a change pattern in which the TIC periodically changes.

The ultrasound diagnosis apparatus 1000 determines that a movement or a change in size of the object in the ROI periodically occurs (S1340). According to an embodiment, when a difference between the TIC and the fitting curve periodically changes or when the TIC has a pattern in which it periodically changes, the ultrasound image analyzer 120 may determine that the object in the ROI periodically moves or its size periodically changes. According to an embodiment, when it is determined that movement or a change in size of the object periodically occurs, the ultrasound image analyzer 120 may not define frames of the ultrasound image obtained by performing ultrasound imaging of the object as defective frames.

Figure 14:
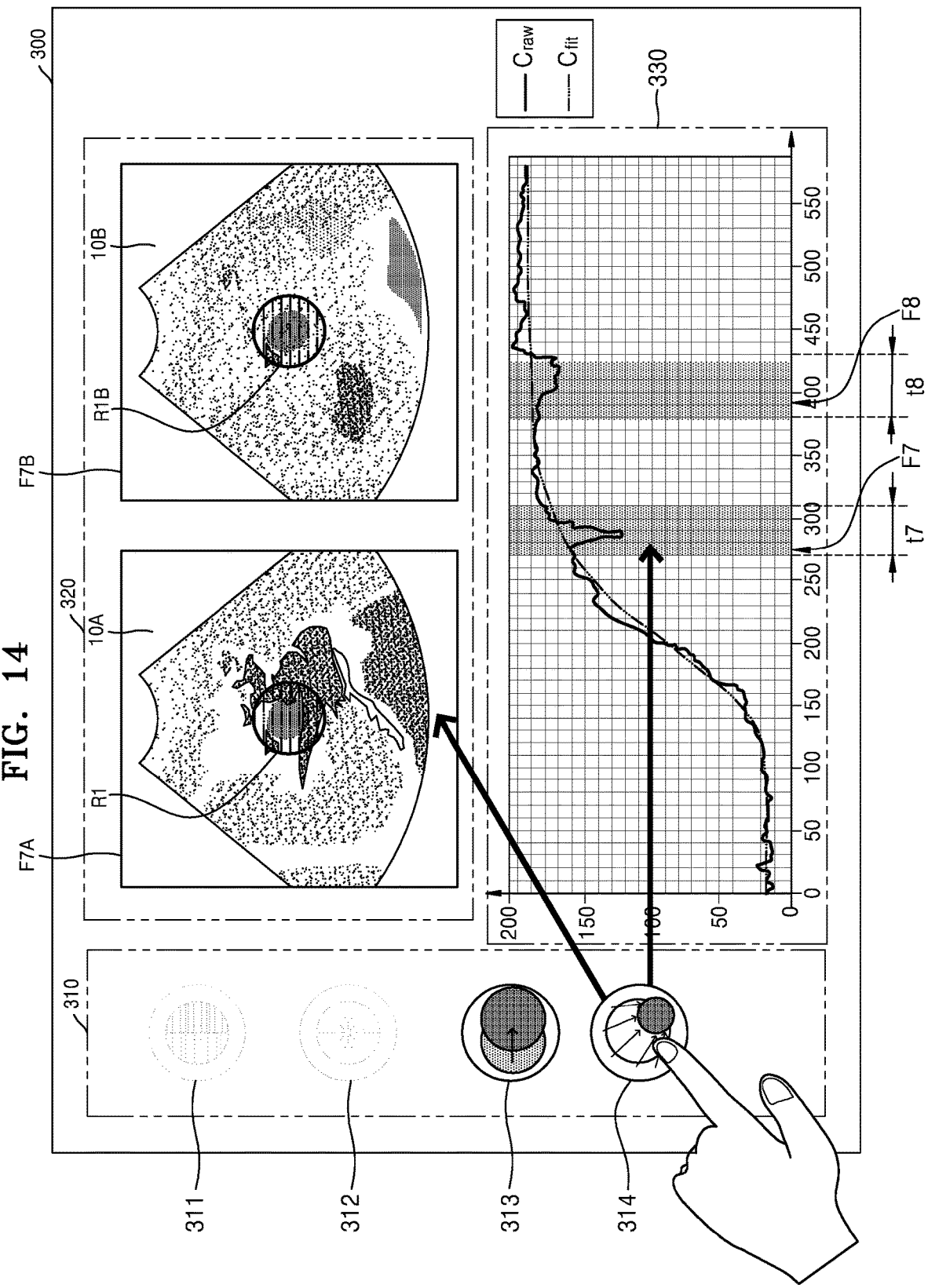
FIG. 14 illustrates a user interface configured to receive a user input for selecting a frame of an ultrasound image related to a motion of an object and a change in size of the object, according to an embodiment.

FIG. 14 illustrates a UI configured to receive a user input for selecting a frame of an ultrasound image related to a movement of an object and a change in size of the object, according to an embodiment.

Referring to FIG. 14, the display 300 is divided into first through third regions 310, 320, and 330. First through fourth UIs 311 through 314 configured to select at least one of the type of movement of an object included in an ROI R1 and a change in size of the object, both of which are analyzed by the ultrasound image analyzer 120, may be displayed in the first region 310. Ultrasound images 10A and 10B of the object may be displayed in the second region 320. A TIC $C_{raw}$ and a fitting curve $C_{fit}$ for each frame of an ultrasound image with respect to the object included in the ROI R1 may be displayed in the third region 330.

The first through fourth UIs 311 through 314 configured to receive a user input for selecting at least one of a periodic movement of the object in the ROI R1, a non-contact between an ultrasound probe and the object, a deviation of the object away from the ROI R1, and a change in size of the object may be displayed in the first region 310. According to an embodiment, the user input unit 200 may display the first through fourth UIs 311 through 314. According to an embodiment, the user input unit 200 may be a touch screen configured to receive a user touch input or may be formed integrally with the display 300. According to an embodiment, the first through fourth UIs 311 through 314 may be GUIs. In detail, the first through fourth UIs 311 through 314 may be configured to respectively receive user inputs related to a periodic movement of the object, a non-contact between an ultrasound probe and the object, a deviation of the object away from the ROI R1, and a change in size of the object.

When a user input for selecting at least one of the first through fourth UIs 311 through 314 displayed in the first region 310 is received, a frame of an ultrasound image related to at least one of the type of movement of the object and a change in size of the object may be displayed in the second region 320. When a user input for selecting the fourth UI 314 displayed in the first region 310 is received, frames F7A and F7B of an ultrasound image captured when a size of the object changes from among successive frames of the ultrasound image with respect to the object included in the ROI R1 may be displayed in the second region 320 based on the user input. Furthermore, in the embodiment, when the user input for selecting the fourth UI 314 is received, a position of the frame F7 captured when the size of the object changes, which is displayed based on the user input, and a time period t7 when the frame F7 is captured may be displayed in the third region 330. The position of the frame F7 and the time interval t7 may be displayed in the third region 330 to overlap the TIC $C_{raw}$. Similarly, when a user input for selecting the third UI 313 is received, a frame F8 of the ultrasound image captured when the object deviates away from the ROI R1 may be displayed in the second region 320 based on the user input. Furthermore, a position of the frame F8 related to deviation of the object and a time period t8 when the frame F8 is captured may be displayed in the third region 330.

Each of the first through fourth UIs 311 through 314 displayed in the first region 310 may be activated when a frame of the ultrasound image related to each of the first through fourth UIs is detected. According to an embodiment, the first UI 311 may be a GUI configured to receive a user input related to a periodic change in size of the object in the ROI R1 and may be deactivated when the periodic change in size of the object is not detected by the ultrasound image analyzer 120. Similarly, the second UI 312 may be a GUI configured to receive a user input related to a non-contact between the ultrasound probe and the object, and may be deactivated when a frame of the ultrasound image captured when the ultrasound probe is not in contact with the object is not detected by the ultrasound image analyzer 120.

According to an embodiment, the ultrasound images 10A and 10B may be a CEUS image and a B mode ultrasound image, respectively, and may be displayed simultaneously in the second region 320. However, embodiments are not limited thereto, and only the ultrasound image 10A that is a CEUS image may be displayed in the second region 320.

According to an embodiment, in examination using a CEUS image, the ultrasound diagnosis apparatus 1000 may detect, based on a difference between a TIC $C_{raw}$ and a fitting curve $C_{fit}$ for each frame of an ultrasound image, a defective frame of the ultrasound image generated due to a movement of the object in the ROI R1, a change in size of the object, and a non-contact between the object and an ultrasound probe and display the detected defective frame, thereby allowing the user to easily delete the defective frame. This configuration may shorten the time required for the examination and increase reliability and robustness in examination results. Furthermore, according to an embodiment, by analyzing a deviation of an object such as a tumor, a periodic movement of the tumor, a change in size of the tumor, and non-contact between the tumor and an ultrasound probe and providing a UI configured to receive a user input for selecting at least one of the analyzed type of movement of the tumor and change in size of the tumor, it is possible for a user to directly select or delete a defective frame and thus increase user convenience.

Figure 15:
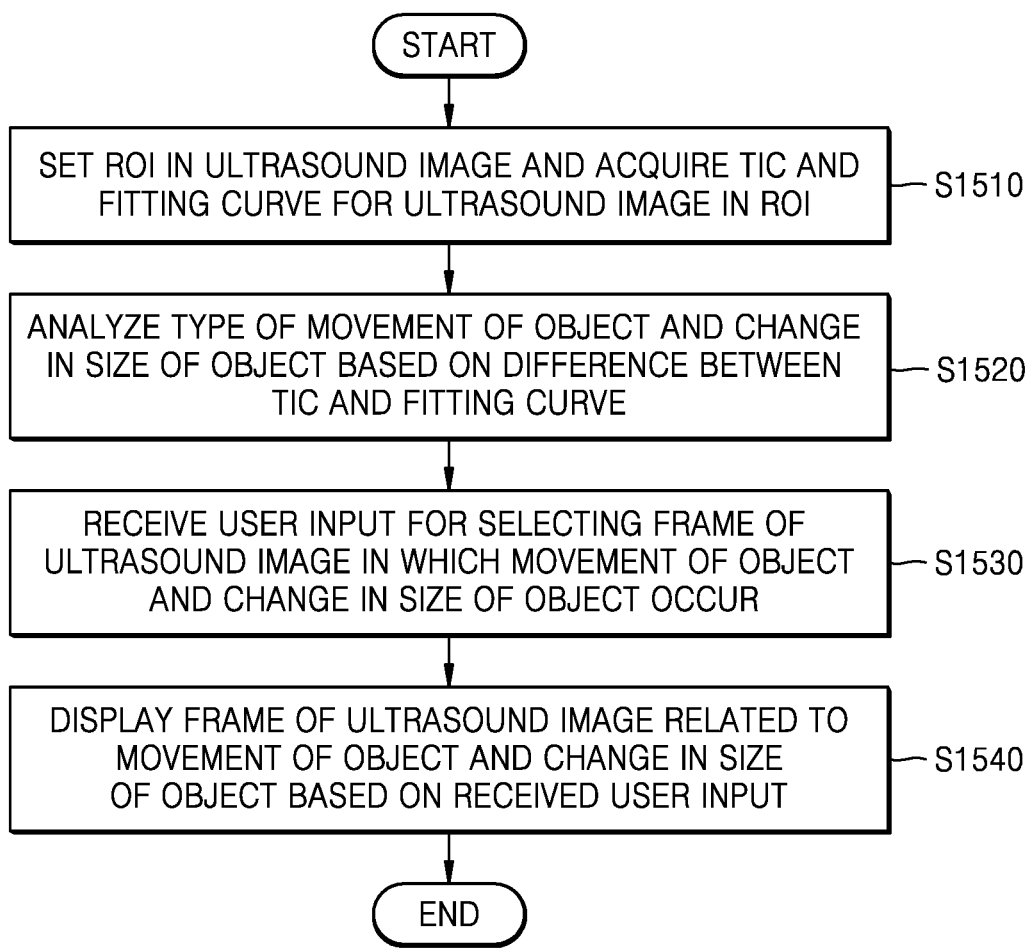
FIG. 15 is a flowchart of a method of displaying a frame of an ultrasound image based on a user input for selecting a frame of an ultrasound image related to a type of motion of an object and a change in size of the object, according to an embodiment.

FIG. 15 is a flowchart of a method of displaying a frame of an ultrasound image based on a user input for selecting a frame of an ultrasound image related to the type of a movement of an object and a change in size of the object, according to an embodiment.

The ultrasound diagnosis apparatus 1000 sets an ROI in an ultrasound image and acquires a TIC and a fitting curve for each ultrasound image frame in the ROI (S1510). Since operations of setting an ROI and generating a TIC and a fitting curve respectively correspond to operations S310 and S320 described with reference to FIG. 3, the same descriptions already provided with respect to FIG. 3 will be omitted below.

The ultrasound diagnosis apparatus 1000 analyzes the type of a movement of an object and a change in size of the object based on a difference between the TIC and the fitting curve (S1520). According to an embodiment, the ultrasound image analyzer 120 may analyze, based on a difference value curve representing a difference between the TIC and the fitting curve for each ultrasound image frame, a deviation of the object away from the ROI, a periodic movement of the object, a change in size of the object, and non-contact between an ultrasound probe and the object. According to an embodiment, the ultrasound image analyzer 120 may determine whether a difference between the TIC and the fitting curve exceeds a threshold value and determine a defective frame from among frames of the ultrasound image.

The ultrasound diagnosis apparatus 1000 receives a user input for selecting a frame of the ultrasound image in which at least one of the movement of the object and the change in size of the object occur (S1530). According to an embodiment, the user input unit 200 may receive a user input for selecting frames of the ultrasound image related to the type of movement of the object and a change in size of the object that are analyzed by the ultrasound image analyzer 120. According to an embodiment, the user input unit 200 may display a GUI configured to receive a user input for selecting a frame of the ultrasound image related to at least one of a movement of the object in the ROI, a change in size of the object, a periodic movement of the object, and a non-contact between the ultrasound probe and the object. According to an embodiment, the GUI may be displayed on the display 300.

The ultrasound diagnosis apparatus 1000 displays the frame of the ultrasound image related to the movement of the object and the change in size of the object based on the user input (S1540). According to an embodiment, when a user input for selecting a frame of the ultrasound image related to at least one of movement of the object, a change in size of the object, a periodic movement of the object, and a non-contact between the ultrasound probe and the object is received, the display 300 may display the frame of the ultrasound image related to the at least one based on the user input. Furthermore, the frame of the ultrasound image related to the movement of the object and the change in size of the object may be displayed together with a TIC and a fitting curve. According to an embodiment, a position of the frame of the ultrasound image may be displayed to overlap the TIC.

Figure 16:
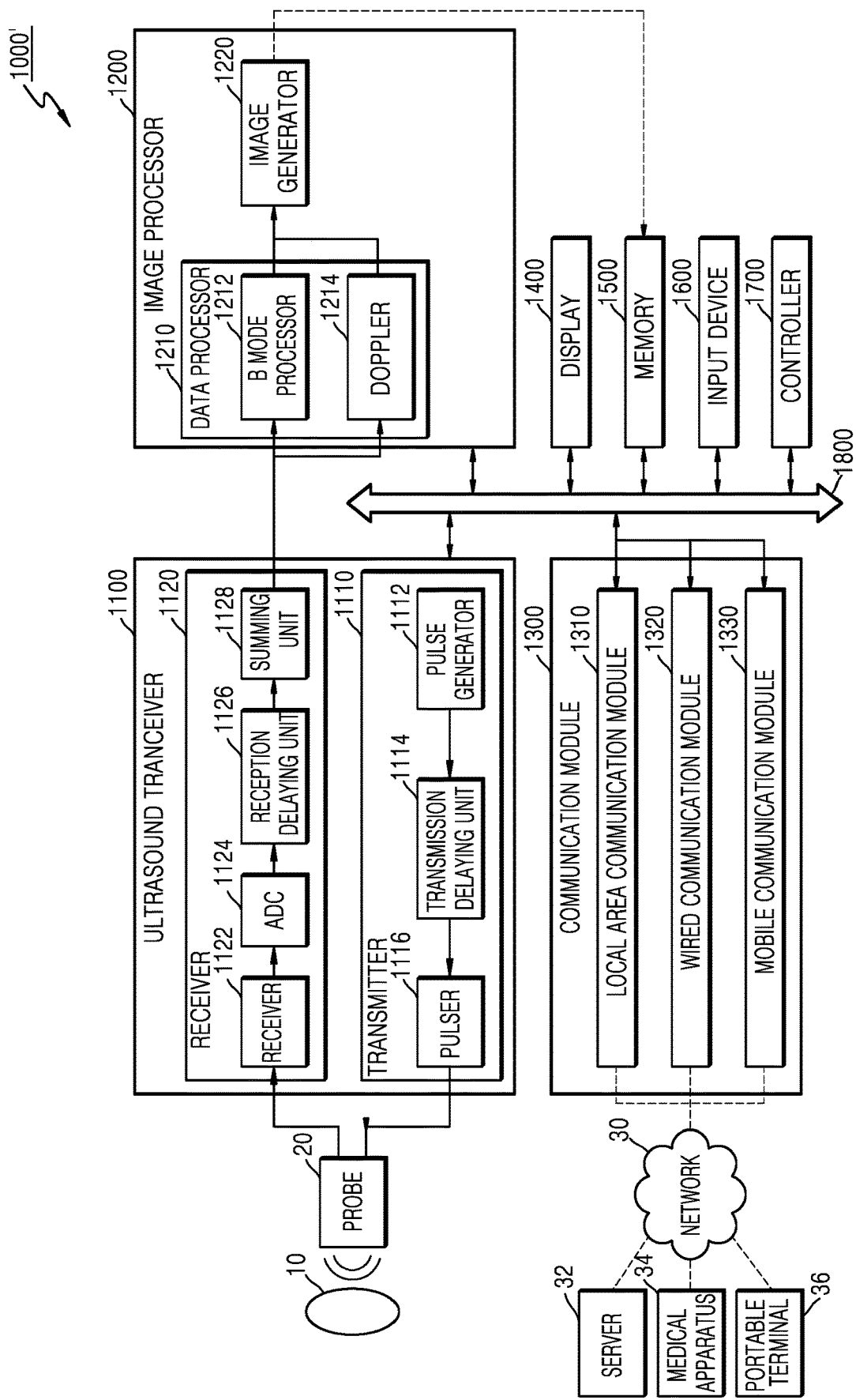
FIG. 16 is a block diagram of a configuration of an ultrasound diagnosis apparatus according to an embodiment.

FIG. 16 is a block diagram of a configuration of an ultrasound diagnosis apparatus 1000' according to an embodiment. Referring to FIG. 16, the ultrasound diagnosis apparatus 1000 may include a probe 20, an ultrasound transceiver 1100, an image processor 1200, a communication module 1300, a display 1400, a memory 1500, an input device 1600, and a controller 1700, which may be connected to one another via buses 1800. The ultrasound diagnosis apparatus 1000 of FIG. 1 may include the same components as those of the ultrasound diagnosis apparatus 1000' of FIG. 16. According to an embodiment, the image processor 1200, the input device 1600, and the display 1400 may respectively correspond to the ultrasound image processor 110, the user input unit 200, and the display 300 described with reference to FIG. 1.

The ultrasound diagnosis apparatus 1000' may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1126. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000' on a screen image via a graphical user interface (GUI). In addition, the ultrasound diagnosis apparatus 1000' may include two or more displays 1400 according to embodiments.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000'. For example, the memory 1500 may store medical data related to diagnosis of an object, such as ultrasound data and an ultrasound image that are input or output, and may also store algorithms or programs which are to be executed in the ultrasound diagnosis apparatus 1000'.

The memory 1500 may be any of various storage media, e.g., a flash memory, a hard disk drive, EEPROM, etc. Furthermore, the ultrasound diagnosis apparatus 1000' may utilize web storage or a cloud server that performs the storage function of the memory 1500 online.

The input device 1600 refers to a means via which a user inputs data for controlling the ultrasound diagnosis apparatus 1000'. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000'. In other words, the controller 1700 may control operations among the probe 20, the ultrasound transceiver 1100, the image processor 1200, the communication module 1300, the display 1400, the memory 1500, and the input device 1600 shown in FIG. 16.

All or some of the probe 20, the ultrasound transceiver 1100, the image processor 1200, the communication module 1300, the display 1400, the memory 1500, the input device 1600, and the controller 1700 may be implemented as software modules. Also, at least one of the ultrasound transmission/reception unit 1100, the image processor 1200, and the communication module 1300 may be included in the control unit 1700; however, the inventive concept is not limited thereto.

FIG. 17 is a block diagram showing a configuration of a wireless probe 2000 according to an embodiment. As described above with reference to FIG. 16, the wireless probe 2000 may include a plurality of transducers, and, according to embodiments, may include some or all of the components of the ultrasound transceiver 2100 shown in FIG. 16.

The wireless probe 2000 according to the embodiment shown in FIG. 17 includes a transmitter 2100, a transducer 2200, and a receiver 2300. Since descriptions thereof are given above with reference to FIG. 16, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 1000' shown in FIG. 16.

The embodiments of the present disclosure may be written as computer programs and may be implemented in general-use digital computers that execute the programs using a non-transitory computer-readable recording medium.

Examples of the non-transitory computer-readable recording medium include magnetic storage media (e.g., ROM, floppy disks, hard disks, etc.), optical recording media (e.g., CD-ROMs, or DVDs), etc.

While one or more embodiments of the present disclosure have been described with reference to the figures, it will be understood by those of ordinary skill in the art that various changes in form and details may be made therein without departing from the spirit and scope of the present disclosure as defined by the following claims.

What is claimed is:

1. An ultrasound diagnosis apparatus for analyzing a contrast enhanced ultrasound image with respect to an object to which an ultrasound contrast medium has been administered, the contrast enhanced ultrasound image being obtained by transmitting ultrasound waves to the object and receiving echo signals reflected from the object, the ultrasound diagnosis apparatus comprising:
   a processor configured to:
      acquire a time intensity curve representing an intensity value of a region of interest (ROI) of ultrasound image frames and a fitting curve representing a tendency of the time intensity curve according to a preset mathematical model,
      calculate a difference between the time intensity curve and the fitting curve for each of the ultrasound image frames, and
      determine a defective frame related to a movement or a change in size of the object in the ROI from among the ultrasound image frames when the calculated difference exceeds a threshold value for each of the ultrasound image frames; and
   a user input interface configured to display a graphical user interface (GUI) related to the defective frame.

2. The ultrasound diagnosis apparatus of claim 1, wherein the processor is further configured to determine the defective frame by analyzing at least one of a simple movement that is a temporary deviation of an anatomical structure in the object away from the ROI, a periodic movement that is a periodic deviation of the anatomical structure in the object away from the ROI, and the change in size of the object in the ROI.

3. The ultrasound diagnosis apparatus of claim 1, wherein the processor is further configured to recognize a state in which an ultrasound probe is not in contact with the object.

4. The ultrasound diagnosis apparatus of claim 1, wherein the processor is further configured to analyze a type of the movement of the object and the change in size of the object based on the difference between the time intensity curve and the fitting curve, and the user input interface displays, based on a result of the analyzing, the GUI corresponding to each of the type of movement of the object, the change in size of the object, and a state of non-contact between an ultrasound probe and the object.

5. The ultrasound diagnosis apparatus of claim 1, further comprising a display configured to display the defective frame.

6. The ultrasound diagnosis apparatus of claim 1, wherein the processor is further configured to determine that an anatomical structure in the object has periodically deviated away from the ROI when the calculated difference periodically exceeds the threshold value.

7. The ultrasound diagnosis apparatus of claim 1, wherein the threshold value is determined based on an average of differences between the time intensity curve and the fitting curve for each of the ultrasound image frames and a standard deviation of the differences.

8. The ultrasound diagnosis apparatus of claim 1, further comprising a display configured to display the time intensity curve, the fitting curve, a difference curve representing the difference between the time intensity curve and the fitting curve for each of the ultrasound image frames, and a threshold curve representing the threshold value for each of the ultrasound image frames.

9. The ultrasound diagnosis apparatus of claim 1, wherein the processor is further configured to:
   set an additional ROI, which is larger than and includes the ROI, in each of the ultrasound image frames,
   acquire a time intensity curve for each of the ultrasound image frames within the additional ROI, and
   analyze a change in intensity values of each of the ultrasound image frames within the additional ROI based on the acquired time intensity curve for the additional ROI.

10. The ultrasound diagnosis apparatus of claim 9, wherein the processor is further configured to analyze movement of the object included in the additional ROI and a change in size of the object based on the result of the analyzing the change in intensity values of each of the ultrasound image frames within the additional ROI.

11. A method of analyzing an ultrasound image with respect to an object to which an ultrasound contrast medium has been administered, the ultrasound image being obtained by transmitting ultrasound waves to the object and receiving echo signals reflected from the object, the method comprising:

acquiring a time intensity curve representing an average of intensity values of a region of interest (ROI) of ultrasound image frames and a fitting curve representing a tendency of the time intensity curve according to a preset mathematical model;

calculating a difference between the acquired time intensity curve and the fitting curve for each of the ultrasound image frames;

determining a defective frame related to a movement or a change in size of the object in the ROI from among the ultrasound image frames when the calculated difference exceeds a threshold value for each of the ultrasound image frames; and displaying a graphical user interface (GUI) related to the defective frame.

12. The method of claim 11, further comprising:

receiving, via a user interface, a user input for selecting at least one of the type of movement of the object and the change in size of the object; and displaying, based on the user input, the defective frame.

13. The method of claim 11, wherein the determining the defective frame comprises determining the defective frame by analyzing at least one of a simple movement that is a temporary deviation of an anatomical structure in the object away from the ROI, a periodic movement that is a periodic deviation of the anatomical structure in the object away from the ROI, and the change in size of the object in the ROI.

14. The method of claim 11, further comprising:

recognizing a state in which an ultrasound probe is not in contact with the object.

15. The method of claim 14, wherein the recognizing of the state in which the ultrasound probe is not in contact with the object comprises:

determining at least one ultrasound image frame from among the ultrasound image frames at which the time intensity curve for the ultrasound image frame has a value of 0; and determining the at least one ultrasound image frame as the defective frame captured when the ultrasound probe is not in contact with the object.

16. The method of claim 11, wherein the threshold value is determined based on an average of differences between the time intensity curve and the fitting curve for each of the ultrasound image frames and a standard deviation of the differences.

17. The method of claim 11, further comprising:

setting an additional ROI, which is larger than and includes the ROI, in each of the ultrasound image frames;

acquiring a time intensity curve for each of the ultrasound image frames included in the additional ROI; and analyzing a change in intensity values of each of the ultrasound image frames included in the additional ROI based on the acquired time intensity curve for the additional ROI.

18. The method of claim 17, further comprising:

analyzing the movement of the object and the change in size of the object based on a result of the analyzing of the change in intensity values of each of the ultrasound image frames included in the additional ROI.

19. The method of claim 17, further comprising:

analyzing, based on the acquired time intensity curve for the additional ROI, whether the intensity values of each of the ultrasound image frames included in the additional ROI periodically change.

20. The method of claim 11, wherein the displaying of the user interface comprises displaying a highlight associated with the defective frame on the time intensity curve at a position where an intensity is associated with the defective frame to distinguish the defective frame from other ultrasound image frames.

21. The method of claim 11, further comprising displaying an ultrasound image from among the ultrasound image frames selected based on a user input.

22. A non-transitory computer-readable recording medium having recorded thereon a program for executing the method of claim 11 on a computer.

* * * * *